United States Patent
Xie et al.

(10) Patent No.: US 9,751,884 B2
(45) Date of Patent: Sep. 5, 2017

(54) N-ARYL UNSATURATED FUSED RING TERTIARY AMINE COMPOUNDS, PREPARATION METHOD AND ANTI-TUMOR APPLICATIONS THEREOF

(71) Applicant: Institute of Pharmacology and Toxicology Academy of Military Medical Sciences P.L.A. China, Beijing (CN)

(72) Inventors: Lan Xie, Beijing (CN); Xiaofeng Wang, Beijing (CN); Kuo-Hsiung Lee, Chapel Hill, NC (US)

(73) Assignee: Institute of Pharmacology and Toxicology Academy of Military Medical Sciences P.L.A. China, Beijing (CN)

( * ) Notice: Subject to any disclaimer, the term of this patent is extended or adjusted under 35 U.S.C. 154(b) by 0 days.

(21) Appl. No.: 14/403,750

(22) PCT Filed: May 30, 2013

(86) PCT No.: PCT/CN2013/076457
§ 371 (c)(1),
(2) Date: Nov. 25, 2014

(87) PCT Pub. No.: WO2013/178075
PCT Pub. Date: Dec. 5, 2013

(65) Prior Publication Data
US 2015/0141407 A1 May 21, 2015

(30) Foreign Application Priority Data
May 31, 2012 (CN) .......................... 2012 1 0176454

(51) Int. Cl.
| C07D 473/40 | (2006.01) |
| C07D 403/04 | (2006.01) |
| C07D 473/32 | (2006.01) |
| C07D 215/20 | (2006.01) |
| C07D 473/00 | (2006.01) |
| C07D 401/04 | (2006.01) |
| C07D 413/04 | (2006.01) |
| C07D 473/34 | (2006.01) |

(52) U.S. Cl.
CPC ......... *C07D 473/40* (2013.01); *C07D 215/20* (2013.01); *C07D 401/04* (2013.01); *C07D 403/04* (2013.01); *C07D 413/04* (2013.01); *C07D 473/00* (2013.01); *C07D 473/32* (2013.01); *C07D 473/34* (2013.01)

(58) Field of Classification Search
CPC .. C07D 473/40; C07D 401/04; C07D 403/04; C07D 413/04; C07D 215/20; C07D 473/00; C07D 473/32
See application file for complete search history.

(56) References Cited

U.S. PATENT DOCUMENTS

| 4,532,333 A | 7/1985 | Glamkowski et al. |
| 5,863,924 A | 1/1999 | Berger et al. |
| 5,958,934 A | 9/1999 | Berger et al. |
| 7,205,306 B2 | 4/2007 | Arvanitis et al. |
| 9,139,590 B2 | 9/2015 | Gangjee |
| 2009/0069341 A1 | 3/2009 | Chene et al. |
| 2014/0073628 A1* | 3/2014 | Rice ..................... C07D 413/04 514/210.21 |
| 2014/0179689 A1* | 6/2014 | Lawrence .............. A61K 45/06 514/218 |
| 2014/0315886 A1* | 10/2014 | Suzuki ................. C07D 487/04 514/210.21 |

FOREIGN PATENT DOCUMENTS

| CN | 1141633 A | 1/1997 |
| CN | 1187129 A | 7/1998 |

(Continued)

OTHER PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Meneyrol. J.. et al.,"A Facile Route for the Preparation of N-Phenyl Tetrahydroquinolines and Tetrahydroisoquinolines," Synthetic Communications 31(7);987-992, Informa UK Ltd., England {2001).
Extended European Search Report in European Application No. 13 79 8070, European Patent Office, Germany, mailed Nov. 25, 2015, 9 pages.

(Continued)

Primary Examiner — Kristin Vajda
(74) Attorney, Agent, or Firm — Sterne, Kessler, Goldstein & Fox P.L.L.C.

(57) ABSTRACT

The present invention relates to a compound of Formula I or a pharmaceutically acceptable salt thereof, its preparation method, a pharmaceutical composition comprising the compound, and its use in manufacture of a medicament for treatment of a disease or disorder, wherein $R_1$, $R_2$, $R_5$, $R_6$, X, Y, Q, W, $n_1$ and $n_2$ are defined as those stated in the description.

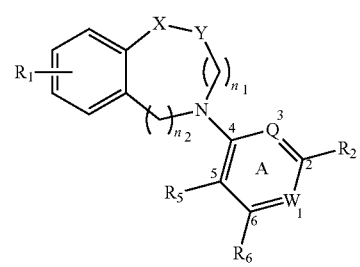

I

5 Claims, No Drawings

(56) References Cited

FOREIGN PATENT DOCUMENTS

| | | |
|---|---|---|
| CN | 1527710 A | 9/2004 |
| CN | 101027054 A | 8/2007 |
| CN | 102786512 A | 11/2012 |
| DE | 2165310 A1 | 7/1973 |
| EP | 0 901 474 B1 | 4/2006 |
| FR | 1572121 A | 6/1969 |
| JP | S60224673 A | 10/1985 |
| JP | H8508290 A | 9/1996 |
| JP | 2001525794 A | 12/2001 |
| JP | 2003321451 A | 11/2003 |
| JP | 2004533447 A | 11/2004 |
| JP | 2008508217 A | 3/2008 |
| JP | 2011116663 A | 6/2011 |
| JP | 2014504644 A | 2/2014 |
| JP | 2014522837 A | 9/2014 |
| WO | WO-9422850 A1 | 10/1994 |
| WO | WO 95/23141 A1 | 8/1995 |
| WO | WO 96/39145 A | 12/1996 |
| WO | WO-9744326 A1 | 11/1997 |
| WO | WO 99/06396 A1 | 2/1999 |
| WO | WO 02/092090 A1 | 11/2002 |
| WO | WO 2004/013091 A2 | 2/2004 |
| WO | WO 2006/010594 A1 | 2/2006 |
| WO | WO 2007/109045 A1 | 9/2007 |
| WO | WO 2009/145357 A1 | 12/2009 |
| WO | WO 2010/151737 A2 | 12/2010 |
| WO | WO 2012/106522 A2 | 8/2012 |
| WO | WO-2013003586 A1 | 1/2013 |

OTHER PUBLICATIONS

English-language translation of Japanese Publication No. 2003-321451, published Nov. 11, 2003; 42 pages.

Sano, H., et al., "Design and Synthesis of Subtype-selective Cyclooxygenase (COX) Inhibitors Derived from Thalidomide," Bioorganic & Medicinal Chemistry 13(9):3079-3091, Elsevier Ltd., England (2005).

International Search Report (ISR) for PCT/CN2013/076457; I.A. fd: May 30, 2013, mailed Aug. 29, 2013, State Intellectual Property Office of the P.R. China, Beijing, China.

International Preliminary Report on Patentability (IPRP) including the Written Opinion of the International Searching Authority (PCT Rule 44bis) for PCT/CN2013/076457; I.A. fd: May 30, 2013, issued Dec. 2, 2014, by the International Bureau of WIPO, Geneva, Switzerland.

STN International, Registry Search, CAS, STN on the Web, 8 pages, Columbus, OH, Aug. 14, 2011.

\* cited by examiner

N-ARYL UNSATURATED FUSED RING TERTIARY AMINE COMPOUNDS, PREPARATION METHOD AND ANTI-TUMOR APPLICATIONS THEREOF

TECHNICAL FIELD

The present invention relates to an N-aryl unsaturated fused ring tertiary amine compound possessing multiple antitumor activities or a pharmaceutical salt thereof, its preparation method, a pharmaceutical composition containing the compound, and its use in manufacture of an antitumor medicament.

BACKGROUND ART

Tumors, especially cancers, are one of the most serious diseases having strong impact on life of people. Since 1970s, the incidence and mortality rate of cancers in China are on the increase. In urban residents, cancers take the first place of cause of death. According to statistics, 1 of 4 deaths dies of cancer in China. In recent years, based on the incidence mechanism of cancer in molecular level, the international pharmaceutical companies develop many novel anti-cancer drugs and therapeutic methods, such as inhibitors targeting cell signal transducers or new vessels, drugs against metastasis or drug-resistance, differentiation inducers, targeting therapy, improving or regulating body immune function, and gene therapy. However, the existing antitumor and anticancer drugs still cannot meet clinical requirements. In addition, the treatment of solid tumor which occupies 90% or more of malignant tumor and has most serious impact on human life and health achieves far from satisfactory effects. Thus, it is still a hot spot in pharmaceutical research to find and develop new high-performance low-toxic antitumor and anticancer drugs.

CONTENTS OF THE INVENTION

The inventors of the present invention find a series of N-aryl unsaturated fused ring tertiary amine compounds showing significant anticancer activity and broad-spectrum or good selectivity (partial data are shown in Table 1) via inhibition activity tests of synthesized small molecular compounds in many human cancer cell lines (A459, DU145, KB, KB-VIN). The anticancer activities of these compounds are not reported yet. Intensive research on these compounds would lead to develop new antitumor or anticancer drugs with novel structure.

Hence, the first aspect of the present invention relates to a compound of Formula I or a pharmaceutical salt thereof:

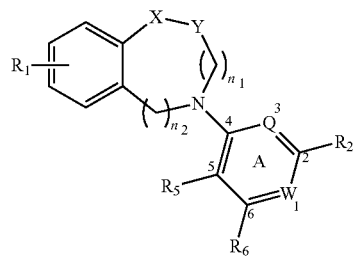

I wherein,

X and Y each independently are —O—, —S—, —S(O)—, —S(O)$_2$—, —C(O)—, —NR'—, —CHOR'—, —CHNHR'—, —CHNR'R''— or —CR'R''—; or X and Y together form —CH=CH—; wherein R' and R'' each independently are H, C$_{1-6}$ alkyl, C$_{2-6}$ alkenyl, C$_{2-6}$ alkynyl, C$_{3-6}$ cycloalkyl, C$_{1-6}$ alkoxyl, C$_{1-6}$ alkylamino, hydroxyl C$_{1-6}$ alkyl, C$_{1-6}$ halogenated alkyl, hydroxyl, acyl, aryl or heteroaryl; and when R' and R'' form a chiral center at substitution site, the compound of Formula I can be a single R, S configuration or a racemate;

R$_1$ represents 1, 2, 3 or 4 substituents optionally existing on the benzene ring, independently being H, alkyl, alkoxyl, halogen, acyl, alkenyl, alkynyl, hydroxyl, cyano, amino, alkylamino, dialkylamino, cyano alkyl, hydroxyl alkyl, halogenated alkyl, acylamino, alkylthio, cycloalkyl, heterocycloalkyl, aryl or heteroaryl;

R$_2$ is alkyl, alkoxyl, halogen, acyl, alkenyl, alkynyl, hydroxyl, cyano, amino, alkylamino, dialkylamino, acylamino, alkylthio, cycloalkyl, hydroxyl alkyl, halogenated alkyl, cyano alkyl, heterocycloalkyl, aryl or heteroaryl;

Q and W each independently are N or CR; wherein R is H, halogen (e.g., fluorine, chlorine, bromine, iodine), cyano, amino, hydroxyl, C$_{1-6}$ alkyl, C$_{1-6}$ alkoxyl, hydroxyl C$_{1-6}$ alkyl, C$_{1-6}$ halogenated alkyl, cyano C$_{1-6}$ alkyl, C$_{1-6}$ alkylamino, C$_{1-6}$dialkylamino, C$_{2-6}$ alkenyl or conjugated alkenyl, C$_{2-6}$ alkynyl or conjugated alkynyl, acyl, acylamino, alkylthio, cycloalkyl, heterocycloalkyl, aryl or heteroaryl;

R$_5$ and R$_6$ together with carbon atoms linked to them form 5- or 6-membered saturated, partially unsaturated carbocyclic ring or heterocyclic ring or aromatic ring or aromatic heterocyclic ring, said aromatic ring or aromatic heterocyclic ring forms a conjugated system, wherein the heterocyclic ring or aromatic heterocyclic ring optionally contains 1, 2, 3 or 4 heteroatoms independently selected from N, O or S; the ring is optionally substituted with 1, 2, 3 or 4 R$_3$; or R$_5$ and R$_6$ each independently are H, alkyl, alkoxyl, hydroxyl alkyl, halogen, halogenated alkyl, carboxyl, ester group, acyl, alkenyl, alkynyl, hydroxyl, cyano, amino, alkylamino, dialkylamino, acylamino, alkylthio, cycloalkyl, heterocycloalkyl, aryl or heteroaryl, which are optionally substituted with 1, 2, 3 or 4 R$_3$;

R$_3$ independently is H, C$_{1-6}$ alkyl, C$_{1-6}$ alkoxyl, fluorine, chlorine, bromine, iodine, acyl, C$_{2-6}$ alkenyl, C$_{2-6}$ alkynyl, hydroxyl, cyano, amino, C$_{1-6}$ alkylamino, C$_{1-6}$dialkylamino, acylamino, C$_{1-6}$alkylthio, C$_{3-6}$ cycloalkyl, heterocycloalkyl, C$_{5-10}$aryl or heteroaryl;

n$_1$=0, 1 or 2; and n$_2$=0 or 1.

The second aspect of the present invention relates to a method for preparing the compound of Formula I or a pharmaceutically acceptable salt thereof.

The third aspect of the present invention relates to a pharmaceutical composition comprising at least one of the compounds of Formula I or a pharmaceutically acceptable salt thereof or one or more pharmaceutically acceptable carrier or excipient.

The fourth aspect of the present invention relates to a use of the compound of Formula I or a pharmaceutically acceptable salt thereof in manufacture of a medicament for treatment of a disease or disorder such as a tumor, especially a cancer, or alleviating severity of mentioned disease or disorder, wherein the disease is selected from lung cancer, breast cancer, prostate cancer, gastric cancer, nasopharyngeal cancer, colorectal cancer, ovarian cancer, multiple myeloma, melanin, glioblastoma multiforme, lymph cancer, leukemia, kidney cancer, liver tumor, sarcoma and thyroid cancer and other solid tumors.

The fifth aspect of the present invention relates to a method for treatment of a disease or disorder such as a tumor, especially a cancer, or alleviating severity of mentioned disease or disorder, the method comprising administering to a patient in need of the treatment a therapeutically effective amount of the compound of Formula I or a pharmaceutically acceptable salt thereof, wherein the disease is selected from lung cancer, breast cancer, prostate cancer, gastric cancer, nasopharyngeal cancer, colorectal cancer, ovarian cancer, multiple myeloma, melanin, glioblastoma multiforme, lymph cancer, leukemia, kidney cancer, liver tumor, sarcoma and thyroid cancer and other solid tumors.

The sixth aspect of the present invention relates to at least one of the compound of Formula I or a pharmaceutically acceptable salt thereof, the compound or pharmaceutically acceptable salt thereof is used for treatment of a disease or disorder such as a tumor, especially a cancer, or alleviating severity of the disease or disorder, wherein the disease is selected form lung cancer, breast cancer, prostate cancer, gastric cancer, nasopharyngeal cancer, colorectal cancer, ovarian cancer, multiple myeloma, melanin, glioblastoma multiforme, lymph cancer, leukemia, kidney cancer, liver tumor, sarcoma and thyroid cancer and other solid tumors.

Definition of Substituent

The term "alkyl" used in the text refers to saturated straight or branched monovalent hydrocarbyl, having 1-12 carbon atoms, preferably having 1-10, 1-8, 1-6, 1-4 or 1-3 carbon atoms. Typical examples of "alkyl" include but are not limited to methyl, ethyl, n-propyl, iso-propyl, n-butyl, iso-butyl, tert-butyl, n-pentyl, tert-pentyl, neo-pentyl, hexyl, heptyl, octyl, etc.

The term "alkenyl" used in the text refers to an olefinic unsaturated straight or branched monovalent hydrocarbyl having at least one carbon-carbon double bond (—C═C—), having 2-12 carbon atoms, preferably having 2-10, 2-8, 2-6, 2-4 or 2-3 carbon atoms. Typical examples of "alkenyl" include but are not limited to vinyl, propenyl, allyl, butenyl, 2-butenyl, pentenyl, 2-pentenyl, 1,3-pentadienyl, hexenyl, 2-hexenyl, 1,3-hexadienyl, heptenyl, octenyl, etc.

The term "alkynyl" in the text refers to an acetylenic unsaturated straight or branched monovalent hydrocarbyl having at least one carbon-carbon triple bond (—C≡C—), having 2-12 carbon atoms, preferably having 2-10, 2-8, 2-6, 2-4 or 2-3 carbon atoms. Typical examples of "alkynyl" include but are not limited to ethynyl, propynyl, propargyl, butynyl, pentynyl, hexynyl, heptynyl, octynyl, etc.

The term "amino" used in the text refers to —NH$_2$.

The term "hydroxyl" used in the text refers to —OH.

The term "cyano" used in the text refers to —CN.

The term "carboxyl" used in the text refers to —C(O)OH.

The term "ester group" used in the text refers to group —C(O)OR$^{10}$, wherein R$^{10}$ is selected from alkyl and cycloalkyl as defined in the text. Typical examples of "ester group" include but are not limited to —C(O)OCH$_3$, —C(O)OC$_2$H$_5$ etc.

The term "alkylamino" used in the text refers to group —NHR$^{11}$, wherein R$^{11}$ is selected from alkyl and cycloalkyl as defined in the text. Typical examples of "alkylamino" include but are not limited to methylamino, ethylamino, propylamino, butylamino, cyclopropylamino, etc.

The term "dialkylamino" used in the text refers to group —NR$^{11}$R$^{12}$, wherein R$^{11}$ and R$^{12}$ are independently selected from alkyl and cycloalkyl as defined in the text. Typical examples of "dialkylamino" include but are not limited to dimethylamino, diethylamino, dipropylamino, dibutylamino, etc.

The term "acylamino" used in the text refers to group —NR$^{13}$C(O)R$^{14}$, wherein R$^{13}$ and R$^{14}$ are independently selected from hydrogen and the following groups as defined in the text: alkyl, heteroalkyl, cycloalkyl, heterocycloalkyl, aryl and heteroaryl. Typical examples of "acylamino" include but are not limited to formylamino, acetylamino, cyclohexylcarbonylamino, benzoylamino, benzylcarbonylamino, etc.

The term "alkylthio" used in the text refers to group —SR$^{15}$, wherein R$^{15}$ is alkyl or cycloalkyl as defined in the text. Typical examples of "alkylthio" include but are not limited to methylthio, ethylthio, propylthio, butylthio, cyclohexylthio, etc.

The term "cycloalkyl" used in the text refers to a saturated cyclic hydrocarbyl having 3-12 carbon atoms and having monocyclic ring or dicyclic ring or multicyclic fused ring (including fused or bridged ring system), preferably having 3-10, 3-8, 5-8, 3-6 or 5-6 carbon atoms. Typical examples of "cycloalkyl" include but are not limited to monocyclic ring structure, such as cyclopropyl, cyclobutyl, cyclopentyl, cyclohexyl, cyclopentyl, cyclooctyl, 1-methylcyclopropyl, 2-methylcyclopentyl, 2-methylcyclooctyl; dicyclic ring structure, such as dicyclo[2.2.1]heptyl, and multicyclic ring structure, such as adamantyl, etc.

The term "heterocycloalkyl" used in the text refers to a cycloalkyl as defined in the text that contains one, two or more heteroatoms independently selected from N, O and S. Typical examples of "heterocycloalkyl" include but are not limited to tetrahydrofuryl, tetrahydrothienyl, pyrrolidinyl, piperazinyl, thiazinyl, piperidinyl and morpholinyl, etc.

The term "aryl" used in the text refers to an unsaturated aromatic carbocyclic ring having 5-14 carbon atoms and one monocyclic ring or two or more fused rings. The aryl preferably has 5-10, 5-8 or 5-6 carbon atoms. Typical examples of "aryl" include but are not limited to phenyl, naphthyl and anthryl.

The term "heteroaryl" used in the text refers to a 5-14 membered aromatic heterocyclic ring group, comprising monocyclic aromatic heterocyclic ring and multicyclic aromatic ring in which a monocyclic aromatic ring is fused with one or more other aromatic rings. Heteroaryl contains one or two or more heteroatoms selected from O, S or N. The range of the term "heteroaryl" further covers a group, in which an aromatic ring is fused with one or more non-aromatic rings (carbocyclic ring or heterocyclic ring), and the linking group or site is on the aromatic ring or non-aromatic ring. The heteroaryl preferably has 5-10 ring members, more preferably 5-6 ring members. Typical examples of "heteroaryl" include but are not limited to furyl, imidazolyl, triazolyl, indolyl, tetrazolyl, pyridyl, pteridyl, pyrimidinyl, triazolyl, quinolyl, isoquinolyl, quinazolinyl, quinoxalinyl.

The term "alkoxyl" used in the text refers to the group of —OR$^{16}$, wherein R$^{16}$ is alkyl or cycloalkyl as defined in the text. Typical examples of "alkoxyl" include but are not limited to methoxy, ethoxy, n-propoxy, iso-propoxy, n-butoxy, tert-butoxy, sec-butoxy, n-pentoxy, n-hexoxy, 1,2-dimethylbutoxy, cyclohexoxy, cyclopropoxy.

The term "acyl" used in the text refers to the group of —C(O)R$^{10}$, wherein R$^{10}$ is selected from hydrogen and the following groups as defined in the text: alkyl, heteroalkyl, cycloalkyl, heterocycloalkyl, alkylamino, dialkylamino, aryl or heteroaryl. Typical examples of "acyl" include but are not limited to formyl, acetyl, cyclohexylcarbonyl, benzoyl, etc.

The term "halogen" used in the text refers to fluorine, chlorine, bromine, or iodine, preferably fluorine, chlorine or bromine.

The term "halogenated alkyl" used in the text refers to an alkyl mono- or multi-substituted with halogen, such as fluorine, chlorine, bromine or iodine. Preferred halogenated alkyl is chloromethyl, chloroethyl, dichloroethyl, trifluoromethyl, difluoromethyl, monofluoromethyl, etc.

The term "cyanoalkyl" used in the text refers to an alkyl mono- or multi-substituted with cyano. Preferred cyanoalkyl is cyanomethyl, cyanoethyl, cyanobutyl, etc.

The term "hydroxyalkyl" used in the text refers to an alkyl mono- or multi-substituted with hydroxyl. Preferred hydroxyalkyl is hydroxymethyl, hydroxyethyl, hydroxypropyl, etc.

The groups as defined with the above terms can further be optionally mono- or multi-substituted with —CN, —OH, —NH$_2$, C$_{1-4}$ alkyl, C$_{1-4}$ alkylamino, C$_{1-4}$ alkoxyl or halogen.

When the name of the compound used in the text is not consistent with the chemical structural formula, the chemical structural formula shall prevail.

In a preferable embodiment according to the present invention, $n_2$ is 0, $n_1$ is 1 in Formula I.

In a preferable embodiment according to the present invention, $n_2$ is 1, $n_1$ is 1 in Formula I.

In a preferable embodiment according to the present invention, $n_2$ is 0, $n_1$ is 0 in Formula I.

In a preferable embodiment according to the present invention, $n_2$ is 0, $n_1$ is 1, and X and Y each independently are —CR'R"—, —CHOR'—, —O—, —C(O)—, —NR'—, —S—, —S(O)— or —S(O)$_2$— in Formula I.

In a preferable embodiment according to the present invention, $n_2$ is 0, $n_1$ is 1, and X and Y each independently are —CR'R"—, —CHOR'—, —O—, —C(O)— or —NR'— in Formula I.

In a preferable embodiment according to the present invention, $n_2$ is 1, $n_1$ is 1, and X and Y each independently are —CR'R"—, —CHOR'—, —O—, —C(O)—, —NR'—, —S—, —S(O)— or —S(O)$_2$— in Formula I.

In a preferable embodiment according to the present invention, $n_2$ is 1, $n_1$ is 1, and X and Y each independently are —CR'R"—, —CHOR'—, —O—, —C(O)— or —NR'— in Formula I.

In a preferable embodiment according to the present invention, $n_2$ is 0, $n_1$ is 0, and X and Y each independently are —CR'R"—, —CHOR'—, —O—, —C(O)—, —NR'—, —S—, —S(O)— or —S(O)$_2$— in Formula I.

In a preferable embodiment according to the present invention, $n_2$ is 0, $n_1$ is 0, and X and Y each independently are —CR'R"—, —CHOR'—, —O—, —C(O)— or —NR'— in Formula I.

In a preferable embodiment according to the present invention, R$_5$ and R$_6$ in Formula I form a 5- or 6-membered aromatic ring or aromatic heterocyclic ring optionally substituted with 1 or 2 R$_3$, preferably benzene ring, pyridine ring, pyrimidine ring, pyrazine ring, pyridazine ring, triazine ring, furan ring or thiophene ring, more preferably benzene ring or pyridine ring, most preferably benzene ring.

In another preferable embodiment according to the present invention, R$_5$ and R$_6$ in Formula I are substituents on Ring A.

In another preferable embodiment according to the present invention, R$_5$ in Formula I independently is H, alkyl, alkoxyl or halogen, R$_6$ independently is H, alkyl, alkoxyl, hydroxyl alkyl, halogen, halogenated alkyl, carboxyl, ester group, acyl, hydroxyl, cyano, amino, alkylamino or dialkylamino, which is optionally substituted with 1 or 2 R$_3$.

In another preferable embodiment according to the present invention, R$_5$ in Formula I independently is H, alkyl, alkoxyl or halogen, R$_6$ independently is H, alkyl, alkoxyl, halogen, carboxyl, ester group or acyl, which is optionally substituted with 1 or 2 R$_3$.

In another preferable embodiment according to the present invention, R$_5$ in Formula I independently is H or halogen, R$_6$ independently is alkyl, alkoxyl, halogen, carboxyl, ester group or acyl, which is optionally substituted with 1 or 2 R$_3$.

In a preferable embodiment according to the present invention, X and Y in Formula I each separately are —CR'R"—.

In a preferable embodiment according to the present invention, X and Y in Formula I each separately are —O—.

In a preferable embodiment according to the present invention, X and Y in Formula I each separately are —S—.

In a preferable embodiment according to the present invention, X and Y in Formula I each separately are —CHOR'—.

In a preferable embodiment according to the present invention, X in Formula I is —NR'—, —O— or —S—, and Y is —CR'R"—.

In a preferable embodiment according to the present invention, X and Y in Formula I each independently are —C(O)—, —S(O)—, —S(O)$_2$— or —CR'R"—.

In a preferable embodiment according to the present invention, X and Y in Formula I each independently are —C(O)—, —S(O)—, —S(O)$_2$— or —NR'—.

In a preferable embodiment according to the present invention, R$_1$ in Formula I is H, alkyl, alkoxyl, hydroxyl, cyano, amino, alkylamino, dialkylamino, alkylthio or halogen.

In a preferable embodiment according to the present invention, R$_1$ in Formula I is H, alkyl, alkoxyl, hydroxyl or halogen.

In a preferable embodiment according to the present invention, R$_1$ in Formula I is alkoxyl, hydroxyl or halogen.

In a preferable embodiment according to the present invention, R$_1$ in Formula I is alkoxyl or halogen.

In a preferable embodiment according to the present invention, R$_2$ in Formula I is alkyl, alkoxyl, halogen, hydroxyl, cyano, amino, alkylamino, dialkylamino or alkylthio.

In a preferable embodiment according to the present invention, R$_2$ in Formula I is alkyl, alkoxyl, halogen, amino, alkylamino, dialkylamino or alkylthio.

In a preferable embodiment according to the present invention, R$_2$ in Formula I is alkyl, alkoxyl, halogen, amino or alkylamino.

In a preferable embodiment according to the present invention, Q and W in Formula I each separately are N.

In a preferable embodiment according to the present invention, one of Q and W in Formula I independently is N, the other one is CR.

In a preferable embodiment according to the present invention, Q and W in Formula I each separately are CR.

In another preferable embodiment according to the present invention, in Formula I, X and Y each independently are —O—, —S—, —S(O)—, —S(O)$_2$—, —CHOR'—, —C(O)—, —NR'— or —CR'R"—; wherein R' and R" each independently are H, C$_{1-4}$ alkyl, C$_{3-6}$ cycloalkyl, alkoxyl, C$_{1-4}$ alkylamino, hydroxyl, acyl, aryl or heteroaryl;

R$_1$ represents 1 or 2 substituents optionally existing on benzene ring, which independently are H, alkyl, alkoxyl, halogen, hydroxyl, cyano, amino, alkylamino, dialkylamino, alkylthio, cycloalkyl, heterocycloalkyl, aryl or heteroaryl;

R$_2$ is alkyl, alkoxyl, halogen, hydroxyl, cyano, amino, alkylamino, dialkylamino, alkylthio, cycloalkyl, heterocycloalkyl, aryl or heteroaryl;

Q and W each independently are N or CR; R is H, halogen, cyano, amino, hydroxyl, C$_{1-4}$ alkyl, C$_{1-4}$ alkoxyl, hydroxyl $C_{1-4}$ alkyl, cyano $C_{1-4}$ alkyl, $C_{1-4}$ alkylamino, $C_{1-4}$ dialkylamino, alkylthio, cycloalkyl, heterocycloalkyl, aryl or heteroaryl;

$R_5$ and $R_6$ together with carbon atoms linked to them form 5- or 6-membered aromatic ring or aromatic heterocyclic ring, wherein the aromatic heterocyclic ring comprises 1 or 2 heteroatoms each independently selected from N, O or S; the aromatic ring or aromatic heterocyclic ring is optionally substituted with 1 or 2 $R_3$; or $R_5$ independently is H, alkyl, alkoxyl or halogen. $R_6$ independently is H, alkyl, alkoxyl, hydroxyl alkyl, halogen, halogenated alkyl, carboxyl, ester group, acyl, hydroxyl, cyano, amino, alkylamino or dialkylamino, and both of $R_5$ and $R_6$ are optionally substituted with 1 or 2 $R_3$.

$R_3$ independently is H, $C_{1-4}$ alkyl, $C_{1-4}$ alkoxyl, fluorine, chlorine, bromine, iodine, acyl, $C_{2-4}$ alkenyl, $C_{2-4}$ alkynyl, hydroxyl, cyano, amino, $C_{1-4}$ alkylamino, $C_{1-4}$ dialkylamino, acylamino, $C_{1-6}$ alkylthio, $C_{3-6}$ cycloalkyl, heterocycloalkyl, $C_{5-10}$ aryl or heteroaryl;

$n_1$=0, 1 or 2; and $n_2$=0 or 1.

In another preferable embodiment according to the present invention, in Formula I, X and Y each independently are —O—, —CHOR'—, —C(O)—, —CR'R''— or —NR'—; wherein R' and R'' each independently are H, $C_{1-4}$ alkyl, $C_{1-4}$ alkoxyl or hydroxyl;

$R_1$ represents 1 or 2 substituents optionally existing on benzene ring, independently being H, alkyl, alkoxyl, halogen, hydroxyl, cyano, amino, alkylamino or dialkylamino;

$R_2$ is alkyl, alkoxyl, halogen, hydroxyl, cyano, amino, alkylamino or dialkylamino;

Q and W each independently are N or CR; R is H, halogen, cyano, amino, hydroxyl, $C_{1-4}$ alkyl, $C_{1-4}$ alkoxyl, hydroxyl $C_{1-4}$ alkyl, cyano $C_{1-4}$ alkyl, $C_{1-4}$ alkylamino or $C_{1-4}$ dialkylamino;

$R_5$ and $R_6$ together with carbon atoms linked to them form a benzene ring or pyridine ring; the benzene ring or pyridine ring is optionally substituted with 1 or 2 $R_3$; or $R_5$ independently is H, alkyl, alkoxyl or halogen, $R_6$ independently is H, alkyl, alkoxyl, halogen, carboxyl, ester group or acyl, and $R_5$ and $R_6$ each independently are optionally substituted with 1 or 2 $R_3$;

$R_3$ independently is H, $C_{1-4}$ alkyl, $C_{1-4}$ alkoxyl, fluorine, chlorine, bromine, iodine, acyl, $C_{2-4}$ alkenyl, $C_{2-4}$ alkynyl, hydroxyl, cyano, amino, $C_{1-4}$ alkylamino, $C_{1-4}$ dialkylamino, acylamino, $C_{1-4}$ alkylthio, $C_{3-6}$ cycloalkyl, heterocycloalkyl, $C_{5-10}$ aryl or heteroaryl;

$n_1$=0, 1 or 2; and $n_2$=0 or 1.

Preferably, the compound of Formula I of the present invention is selected from:

$N^1$-[4-(2-chloro)quinazolinyl]-6-methoxy-1,2,3,4-tetrahydroquinoline (Compound 1), $N^1$-[4-(2-methyl)quinazolinyl]-6-methoxy-1,2,3,4-tetrahydroquinoline (Compound 2), $N^1$-[4-(2-methoxy)quinazolinyl]-6-methoxy-1,2,3,4-tetrahydroquinoline (Compound 3), $N^1$-[4-(2-methylamino)quinazolinyl]-6-methoxy-1,2,3,4-tetrahydroquinoline (Compound 4), 2-methyl-4-(6-methoxy-7-fluoro-3,4-dihydroquinolin-1(2H)-yl)quinazoline (Compound 5), $N^1$-[4-(2-methyl)quinazolinyl]-6-methyl-1,2,3,4-tetrahydroquinoline (Compound 6), $N^1$-[4-(2-methyl)quinazolinyl]-6-bromo-1,2,3,4-tetrahydroquinoline (Compound 7), 2-methyl-4-[$N^1$-(5-methoxy)indolinyl]quinazoline (Compound 8), $N^2$-[4-(2-methyl)quinazolinyl]-7-methoxy-2,3,4,5-tetrahydro-1H-benzo[c]azepine (Compound 9), $N^1$-[4-(2-chloro)quinazolinyl]-7-methoxy-2,3,4,5-tetrahydro-1H-benzo[b]azepine (Compound 10), $N^1$-[4-(2-methyl)quinazolinyl]-4-hydroxyl-6-methoxy-1,2,3,4-tetrahydroquinoline (Compound 11), $N^1$-[4-(2-chloro)quinazolinyl]-4-ethoxy-6-methoxy-1,2,3,4-tetrahydroquinoline (Compound 12), $N^4$-[4-(2-chloro)quinazolinyl]-7-methoxy-3,4-dihydro-2H-benzo[b][1,4]oxazine (Compound 13), $N^4$-[4-(2-methyl)quinazolinyl]-6-fluoro-7-methoxy-3,4-dihydro-2H-benzo[b][1,4]ox azine (Compound 14), 4-(2-chloroquinazolin-4-yl)-7-methoxy-3,4-dihydro-2H-benzo[b][1,4]thiazine (Compound 15), 4-(2-chloroquinazolin-4-yl)-7-methoxy-3,4-dihydro-2H-benzo[b][1,4]-1-oxythiazine (Compound 16), 4-(2-chloroquinazolin-4-yl)-7-methoxy-3,4-dihydro-2H-benzo[b][1,4]-1,1-dioxythiazine (Compound 17), $N^1$-[4-(2-chloro)quinazolinyl]-6-methoxy-2,3-dihydroquinolin-4(1H)-one (Compound 18), $N^4$-[4-(2-methyl)quinazolinyl]-7-methoxy-3,4-dihydroquinoxalin-2(1H)-one (Compound 19), 6-methoxy-2'-methyl-3,4-dihydro-2H-1,4'-biquinoline (Compound 20), 2-methyl-4-(6-methoxy-3,4-dihydroquinolin-1(2H)-yl)pyrido[2,3-d]pyrimidine (Compound 21), 2-methyl-4-(6-methoxy-3,4-dihydroquinolin-1(2H)-yl)pyrido[3,4-d]pyrimidine (Compound 22), 2-methyl-4-(6-methoxy-3,4-dihydroquinolin-1(2H)-yl)pyrido[4,3-d]pyrimidine (Compound 23), 2-methyl-4-(6-methoxy-3,4-dihydroquinolin-1(2H)-yl)pyrido[3,2-d]pyrimidine (Compound 24), 2-methyl-4-(6-methoxy-3,4-dihydroquinolin-1(2H)-yl)pteridine (Compound 25), $N^1$-[(3-bromo-5-methoxycarbonyl)phenyl]-6-methoxy-1,2,3,4-tetrahydroquinoline (Compound 26), $N^1$-[(3-bromo-5-carboxyl)phenyl]-6-methoxy-1,2,3,4-tetrahydroquinoline (Compound 27), $N^1$-[(3-bromo-5-methylaminoacyl)phenyl]-6-methoxy-1,2,3,4-tetrahydroquinoline (Compound 28), $N^1$-[3-bromo-5-(N-cyclopropylaminoacyl)phenyl]-6-methoxy-1,2,3,4-tetrahydroquinoline (Compound 29), $N^1$-[4-(2-amino-6-chloro)pyrimidinyl]-6-methoxy-1,2,3,4-tetrahydroquinoline (Compound 30), $N^1$-methyl-$N^4$-[4-(2-methyl)quinazolinyl]-7-methoxy-3,4-dihydroquinoxalin-2(1H-one (Compound 31), 2-(N-methylmethylamino)-4-(6-methoxy-1,2,3,4-tetrahydro-1-quinolyl)quinazoline (Compound 32), 2-cyclopropylamino-4-(6-methoxy-1,2,3,4-tetrahydro-1-quinolyl)quinazoline (Compound 33), 2-cyclopentylamino-4-(6-methoxy-1,2,3,4-tetrahydro-1-quinolyl)quinazoline (Compound 34), 2-(3-hydroxylpropylamino)-4-(6-methoxy-1,2,3,4-tetrahydro-1-quinolyl)quinazoline (Compound 35), 4-(6-methoxy-1,2,3,4-tetrahydro-1-quinolyl)quinazoline (Compound 36), 4-(6-methoxy-1,2,3,4-tetrahydro-1-quinolyl)naphthalene (Compound 37), 4-(6-methoxy-1,2,3,4-tetrahydro-1-quinolyl)quinoline (Compound 38), 1-(6-methoxy-1,2,3,4-tetrahydro-1-quinolyl)isoquinoline (Compound 39), 4-(6-methoxy-1,2,3,4-tetrahydro-1-quinolyl)isoquinoline (Compound 40), 8-(6-methoxy-1,2,3,4-tetrahydro-1-quinolyl)quinoline (Compound 41), 6-(6-methoxy-1,2,3,4-tetrahydro-1-quinolyl)purine (Compound 42),
2-fluoro-6-(6-methoxy-1,2,3,4-tetrahydro-1-quinolyl)purine (Compound 43), and
2-amino-6-(6-methoxy-1,2,3,4-tetrahydro-1-quinolyl)purine (Compound 44).

The compound of Formula I according to the present invention can be obtained via the following reaction route:

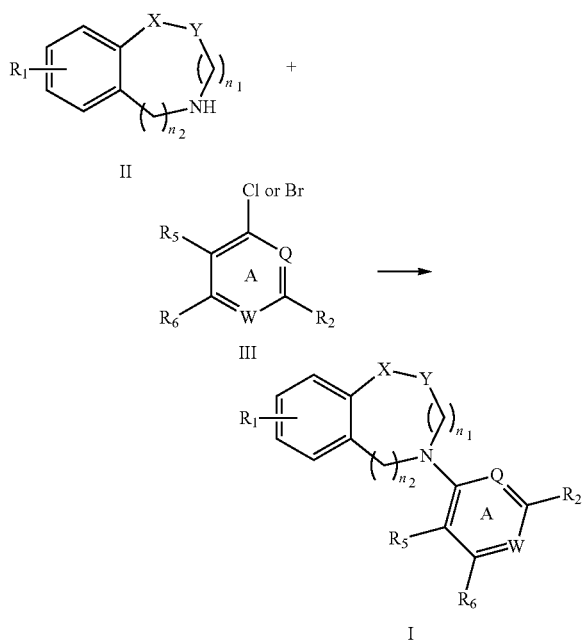

wherein $R_1$, $R_2$, $R_5$, $R_6$, X, Y, Q, W, $n_1$ and $n_2$ are defined as those of the Formula I as above mentioned.

In the presence of an alkali or acid, a substituted halide of Formula III was reacted with a substituted amine compound of Formula II in a solvent to afford a compound of Formula I.

More specifically, in the presence of an alkali in an amount of 2-10 equivalent or an acid in a catalytic amount of up to 2 equivalent (for example, sodium hydride, cesium carbonate, sodium carbonate, sodium bicarbonate, triethylamine, pyridine, N,N-dimethylaminopridine, or potassium carbonate/potassium carbonate, sodium tert-butoxide, cesium carbonate, potassium carbonate; hydrochloric acid, sulfuric acid, hydrobromic acid or acetic acid), and if necessary, under the action of an auxiliary reagent such as cuprous halide, [bis(diphenylphosphino)ferrocene]dichloropalladium/1,1'-bis(diphenylphosphino)ferrocene, palladium acetate, X-Phos, etc., a substituted halide (Formula III) was reacted with a substituted amine compound (Formula II) in a solvent such as DMF, acetonitrile, ethanol, tert-butanol, acetone, isopropanol, methanol, THF, toluene, 1,4-dioxane or DMSO, below the temperature of 200° C. (for example, using ice/water bath or oil bath to control the temperature), for 5 minutes to 24 hours, to provide a compound of Formula I, wherein the inventory molar ratio of the reactants II/III is 1:1 to 1:4.

The reaction can be carried out under condition of microwaves, and the inventory ratio of alkali or acid to the reactants is the same as aforementioned, in a solvent such as DMF, DMSO, tert-butanol, isopropanol, acetone, methanol, ethanol, acetonitrile or 1,4-dioxane, at a temperature of 60-250° C. for 5-60 minutes.

The compounds of the present invention exhibit strong inhibition activity in tests of many cancer cells. As following described, the compounds show equivalent or better inhibition activity in comparison with positive control drug paclitaxel in inhibition activity tests of lung cancer cells (A549), prostate cancer cells (DU145), nasopharyngeal cancer cells (KB) and drug-resistant nasopharyngeal cancer cells (KB-VIN). It is particularly worth noted that some of the compounds have very strong inhibition activity to drug-resistant KB-VIN cells. Hence, the series of compounds of the present invention have a broad anticancer spectrum, and it is promising to develop many new drugs for treatment of tumor or cancers by intensively studying these compounds.

The compounds of the present invention can be used in form of either themselves or their pharmaceutically acceptable salts or solvates. The pharmaceutically acceptable salts of Formula I comprise salts formed with pharmaceutically acceptable inorganic acid or organic acid, or pharmaceutically acceptable inorganic alkali or organic alkali. Examples of suitable acid forms salts include salts formed with hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, pamoic acid, malonic acid, hydroxymaleic acid, phenylacetic acid, glutamic acid, benzoic acid, salicylic acid, fumaric acid, toluene sulfonic acid, methane sulfonic acid, naphthalene-2-sulfonic acid, benzene sulfonic acid, hydroxynaphthoic acid, hydroiodic acid, malic acid, tannic acid. Examples of suitable alkali forms salts comprise salts formed with sodium, lithium, potassium, magnesium, aluminum, calcium, zinc, N,N'-dibenzylethanediamine, chloroprocaine, choline, diethanolamine, ethanediamine, N-methylglucosamine and procaine, etc. When the compounds of the present invention are mentioned in the text, they comprise the compounds of Formula I and their pharmaceutically acceptable salts or solvates.

According to the present invention, the pharmaceutical composition comprises a compound of Formula I and a conventional pharmaceutically acceptable carrier or excipient. The pharmaceutical composition can be administered orally or parenterally. The pharmaceutical composition of the present invention can be processed by conventional method to prepare various dosage forms, including but not limited to tablets, capsules, solutions, suspension, granules or injections, for such as oral or parenteral administration.

It is further pointed out that the dose and usage of the compound of the present invention depend on many factors, including age, body weight, gender, natural health condition, nutritional state, activity potency of compound, administration time, metabolic rate, severity of disease, and subjective judgment of doctor. The preferred dose is 0.01-100 mg/kg body weight/day.

SPECIFIC MODEL FOR CARRYING OUT THE INVENTION

The present invention is further illustrated with the following examples, but is not limited thereto.

Method I: 4-chloro-2-substituted quinazoline (1.0 mmol), 5-methoxyindoline or 6-substituted-1,2,3,4-tetrahydroquinoline or 7-methoxy-2,3,4,5-tetrahydro-1H-benzo[b or c]azepine (1.2 mmol) and sodium bicarbonate (3.0 mmol) were added to anhydrous ethanol (5 ml), reacted at room temperature or under refluxing condition for 1-10 h. After the end of reaction, the reactants were poured into ice-water, adjusted pH with 2N hydrochloric acid to 3, extracted with ethyl acetate, dried with anhydrous sodium sulfate. The solvent was removed under vacuum, and the resultant crude product was separated by silica gel column chromatography (eluent: ethyl acetate and petroleum ether for gradient elution, ethyl acetate 5%-80%).

Method II: 4-chloro-2-methylquinazoline (0.5 mmol), aniline or cyclic secondary amine (0.5 mmol) were added into anhydrous ethanol (5 ml), 1 drop of concentrated hydrochloric acid was added, the resulting mixture was reacted under refluxing for 1-5 h. After the end of reaction, the reactants were poured into ice water, adjusted with saturated NaHCO$_3$ to pH=8, extracted with ethyl acetate, dried with anhydrous sodium sulfate. The solvent was removed under vacuum, and the resultant crude product was separated by silica gel column chromatography (eluent: ethyl acetate and petroleum ether for gradient elution, ethyl acetate 5%-80%).

Example 1: N$^1$-[4-(2-chloro)quinazolinyl]-6-methoxy-1,2,3,4-tetrahydroquinoline (Compound 1, Method I)

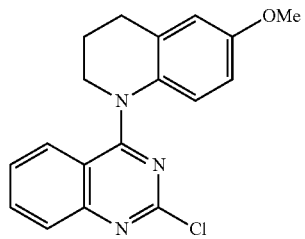 [SMILES: COc1ccc2c(c1)CCCN2c1nc(Cl)nc2ccccc12]

The Compound 1 was obtained after reaction under refluxing for 3 h, which was yellow solid, 282 mg, yield 87%, melting point 136-138° C.; $^1$H NMR (CDCl$_3$): δ ppm 2.12 (2H, m, 3'-CH$_2$), 2.86 (2H, t, J=6.8 Hz, 4'-CH$_2$), 3.81 (3H, s, OCH$_3$), 4.07 (2H, t, J=6.8 Hz, 2'-CH$_2$), 6.55 (1H, dd, J=8.8 Hz and 2.8 Hz, ArH-7'), 6.70 (1H, d, J=8.8 Hz, ArH-8'), 6.81 (1H, d, J=2.8 Hz, ArH-5'), 7.13 (1H, m, ArH-6), 7.32 (1H, dd, J=8.8 Hz and 1.2 Hz, ArH-5), 7.63 (1H, m, ArH-7), 7.78 (1H, dd, J=8.4 Hz and 1.2 Hz, ArH-8). MS m/z (%) 326 (M+H$^+$, 100), 328 (M+3$^+$, 31).

Example 2: N$^1$-[4-(2-methyl)quinazolinyl]-6-methoxy-1,2,3,4-tetrahydroquinoline (Compound 2, Method I)

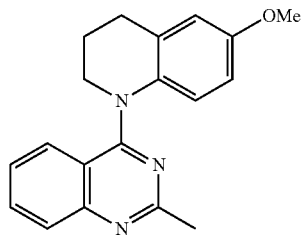 [SMILES: COc1ccc2c(c1)CCCN2c1nc(C)nc2ccccc12]

The compound 2 was obtained after reaction under refluxing for 3 h, which was yellow solid, 242 mg, yield 79%, melting point 134-136° C.; $^1$H NMR (CDCl$_3$): δ ppm 2.11 (2H, m, 3'-CH$_2$), 2.73 (3H, s, CH$_3$), 2.88 (2H, t, J=6.8 Hz, 4'-CH$_2$), 3.79 (3H, s, OCH$_3$), 4.05 (2H, t, J=6.8 Hz, 2'-CH$_2$), 6.53 (1H, dd, J=9.2 Hz and 2.8 Hz, ArH-7'), 6.63 (1H, d, J=8.4 Hz, ArH-8'), 6.78 (1H, d, J=2.8 Hz, ArH-5'), 7.12 (1H, m, ArH-6), 7.32 (1H, dd, J=8.4 Hz and 1.2 Hz, ArH-5), 7.62 (1H, m, ArH-7), 7.79 (1H, d, J=8.0 Hz, ArH-8). MS m/z (%) 306 (M+H$^+$, 100).

Example 3: N$^1$-[4-(2-methoxy)quinazolinyl]-6-methoxy-1,2,3,4-tetrahydro-quinoline (Compound 3)

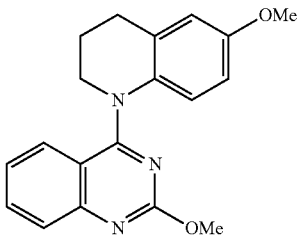 [SMILES: COc1ccc2c(c1)CCCN2c1nc(OC)nc2ccccc12]

2-Chloro-4-(6-methoxy-3,4-dihydroquinolin-1(2H)-yl)quinazoline (81 mg, 0.25 mmol) and NaOCH$_3$ (40 mg, 0.75 mmol) were added into absolute methanol (4.0 ml), reacted under refluxing for 2 h. Insoluble substance was filtered out, silica gel column chromatography (eluent: ethyl acetate and petroleum ether for gradient elution, ethyl acetate 5%-80%) was used for separation to obtain Compound 3, which was amber solid, 71 mg, yield 88%, melting point 161-163° C. $^1$H NMR (CDCl$_3$): δ ppm 2.09 (2H, m, 3'-CH$_2$), 2.85 (2H, t, J=6.8 Hz, 4'-CH$_2$), 3.80 (3H, s, OCH$_3$), 4.03 (2H, t, J=6.8 Hz, 2'-CH$_2$), 4.09 (3H, s, OCH$_3$), 6.53 (1H, dd, J=8.8 Hz and 2.8 Hz, ArH-7'), 6.67 (1H, d, J=8.8 Hz, ArH-8'), 6.79 (1H, d, J=2.8 Hz, ArH-5'), 6.98 (1H, m, ArH-6), 7.32 (1H, dd, J=8.4 Hz and 0.8 Hz, ArH-5), 7.56 (1H, m, ArH-7), 7.68 (1H, d, J=8.4 Hz, ArH-8). MS m/z (%) 322 (M+H$^+$, 100).

Example 4: N$^1$-[4-(2-methylamino)quinazolinyl]-6-methoxy-1,2,3,4-tetrahydro-quinoline (Compound 4)

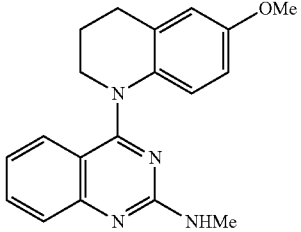 [SMILES: CNc1nc(N2CCCc3cc(OC)ccc32)c2ccccc2n1]

2-Chloro-4-(6-methoxy-3,4-dihydroquinolin-1(2H)-yl)quinazoline (65 mg, 0.2 mmol) and 30% methylamine methanol solution (3 ml) was heated to 100° C. and reacted for 1 h. The reactants were poured into ice-water, extracted with ethyl acetate (3×30 ml), washed with saturated brine, dried by adding anhydrous sodium sulfate. The crude product was separated by silica gel column chromatography (eluent: ethyl acetate and petroleum ether for gradient elution 5%-80%) to obtain Compound 4, which was amber solid, 42 mg, yield 66%, melting point 139-140° C.; $^1$H NMR (CDCl$_3$): δ ppm 2.07 (2H, m, 3'-CH$_2$), 2.85 (2H, t, J=6.8 Hz, 4'-CH$_2$), 3.10 (3H, d, J=5.2 Hz, NCH$_3$), 3.79 (3H, s, OCH$_3$), 3.94 (2H, t, J=6.8 Hz, 2'-CH$_2$), 6.53 (1H, dd, J=9.2 Hz and 2.8 Hz, ArH-7'), 6.67 (1H, d, J=9.2 Hz, ArH-8'), 6.76 (1H, d, J=2.8 Hz, ArH-5'), 6.83 (1H, m, ArH-6), 7.29 (1H, d, J=8.0 Hz, ArH-5), 7.46 (1H, m, ArH-7), 7.52 (1H, d, J=8.0 Hz, ArH-8). MS m/z (%) 321 (M+H$^+$, 100).

Example 5: N¹-[4-(2-methyl)quinazolinyl]-6-methyl-1,2,3,4-tetrahydroquinoline (Method II, Compound 6)

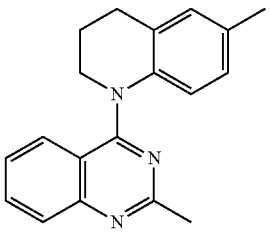 [SMILES: Cc1ccc2c(c1)CCCN2c1nc(C)nc2ccccc12]

Compound 6 was obtained after reaction under refluxing for 1 h, which was yellow solid, 108 mg, yield 75%, melting point 136-138° C.; $^1$H NMR (CDCl$_3$): δ ppm 2.12 (2H, m, 3'-CH$_2$), 2.30 (3H, s, CH$_3$), 2.75 (3H, s, CH$_3$), 2.88 (2H, t, J=2.4 Hz, 4'-CH$_2$), 4.04 (2H, t, J=2.4 Hz, 2'-CH$_2$), 6.55 (1H, d, J=8.4 Hz, ArH-8'), 6.73 (1H, dd, J=8.4 Hz and 2.0 Hz, ArH-7'), 7.03 (1H, s, J=2.8 Hz, ArH-5'), 7.13 (1H, m, ArH-6), 7.32 (1H, dd, J=8.4 Hz and 0.8 Hz, ArH-5), 7.63 (1H, m, ArH-7), 7.81 (1H, d, J=8.0 Hz, ArH-8). MS m/z (%) 290 (M+H⁺, 100).

Example 6: N¹-[4-(2-methyl)quinazolinyl]-6-bromo-1,2,3,4-tetrahydroquinoline (Method II, Compound 7)

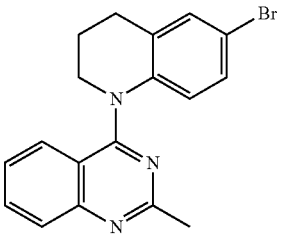 [SMILES: Cc1nc(N2CCCc3cc(Br)ccc32)c2ccccc2n1]

Compound 7 was obtained after reaction under refluxing for 1 h, which was yellow solid, 142 mg, yield 80%, melting point 129-130° C., $^1$H NMR (CDCl$_3$): δ ppm 2.13 (2H, m, 3'-CH$_2$), 2.76 (3H, s, CH$_3$), 2.91 (2H, t, J=6.8 Hz, 4'-CH$_2$), 4.04 (2H, t, J=6.4 Hz, 2'-CH$_2$), 6.49 (1H, d, J=8.8 Hz, ArH-8'), 7.01 (1H, dd, J=8.8 Hz and 2.8 Hz, ArH-7'), 7.22 (1H, m, ArH-6), 7.34 (1H, d, J=2.0 Hz, ArH-5'), 7.46 (1H, dd, J=8.4 Hz and 0.8 Hz, ArH-5), 7.69 (1H, m, ArH-7), 7.85 (1H, d, J=8.4 Hz, ArH-8). MS m/z (%) 354 (M+H⁺, 60), 356 (M+3⁺, 100).

Example 7: 2-Methyl-4-[N¹-(5-methoxy)indolinyl]quinazoline (Method I, Compound 8)

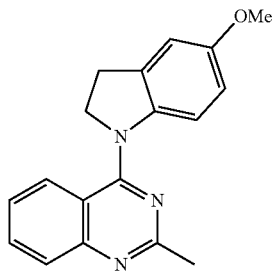 [SMILES: COc1ccc2c(c1)CCN2c1nc(C)nc2ccccc12]

Compound 8 was obtained after reaction at room temperature for 1 h, which was yellow solid, 242 mg, yield 77%, melting point 116-117° C. $^1$H NMR (CDCl$_3$): δ ppm 2.70 (3H, s, CH$_3$), 3.19 (2H, t, J=8.0 Hz, 3'-CH$_2$), 3.81 (3H, s, OCH$_3$), 4.45 (2H, t, J=8.0 Hz, 2'-CH$_2$), 6.69 (1H, dd, J=8.8 Hz and 2.4 Hz, ArH-6'), 6.86 (1H, d, J=2.4 Hz, ArH-4'), 7.37 (2H, m, ArH-7' and ArH-6), 7.73 (1H, t, J=7.6 Hz, ArH-7), 7.84 (1H, d, J=8.4 Hz, ArH-5), 8.03 (1H, d, J=8.4 Hz, ArH-8). MS m/z (%) 292 (M+H⁺, 100).

Example 8: N²-[4-(2-methyl)quinazolinyl]-7-methoxy-2,3,4,5-tetrahydro-1H-benzo[c]azepine (Method I, Compound 9)

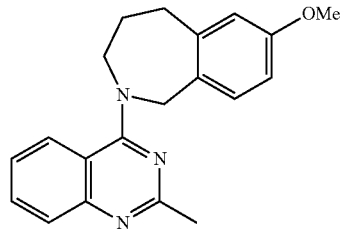 [SMILES: COc1ccc2c(c1)CCCN(c1nc(C)nc3ccccc13)C2]

Compound 9 was obtained after reaction under refluxing for 1 h, which was yellow solid, 236 mg, yield 74%, melting point 125-127° C. $^1$H NMR (CDCl$_3$): δ ppm 2.14 (2H, m, 4'-CH$_2$), 2.65 (3H, s, CH$_3$), 3.03 (2H, t, J=5.6 Hz, 5'-CH$_2$), 3.81 (3H, s, OCH$_3$), 4.09 (2H, t, J=5.2 Hz, 3'-CH$_2$), 4.89 (2H, s, 1'-CH$_2$), 6.73 (1H, dd, J=8.4 Hz and 2.8 Hz, ArH-8'), 6.77 (1H, d, J=2.4 Hz, ArH-6'), 7.24 (1H, d, J=8.0 Hz, ArH-9'), 7.30 (1H, m, ArH-6), 7.65 (1H, m, ArH-7), 7.76 (1H, d, J=8.4 Hz, ArH-5), 7.89 (1H, d, J=8.4 Hz, ArH-8). MS m/z (%) 161 (M−158⁺, 100), 320 (M+H⁺, 55).

Example 9: N¹-[4-(2-chloro)quinazolinyl]-7-methoxy-2,3,4,5-tetrahydro-1H-benzo[b]-azepine (Method I, Compound 10)

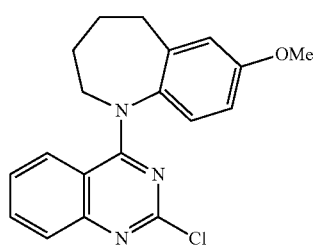 [SMILES: COc1ccc2c(c1)CCCCN2c1nc(Cl)nc2ccccc12]

Compound 10 was obtained after reaction under refluxing for 2 h, which was amber solid, 254 mg, yield 75%, melting point 102-103° C. $^{13}$C NMR (CDCl$_3$): δ ppm 26.03 (4'C), 28.81 (3'C), 34.27 (5'C), 50.93 (2'C), 55.49 (OCH$_3$), 112.37 (6'C), 114.97 (8'C), 116.17 (9'C and 10C), 124.88 (8C), 126.07 (11'C), 127.25 (6C), 127.65 (5C), 138.36 (10'C), 141.15 (7'C), 153.37 (9C), 158.98 (2C), 160.92 (4C). $^1$H NMR (CDCl$_3$): δ ppm 1.94 (2H, m, CH$_2$), 2.05 (2H, m, CH$_2$), 2.79 (2H, m, CH$_2$), 2.94 (2H, m, CH$_2$), 3.86 (3H, s, OCH$_3$), 6.71 (1H, dd, J=8.4 Hz and 2.8 Hz, ArH-8'), 6.72 (1H, d, J=8.4 Hz, ArH), 6.84 (1H, d, J=8.0 Hz, ArH-9'), 6.92 (1H, d, J=2.8 Hz, ArH-8'), 6.97 (2H, t, J=8.0 Hz, ArH-7), 7.55 (1H, d, J=8.0 Hz, ArH-5), 7.71 (1H, d, J=8.0 Hz, ArH-8). MS m/z (%) 340 (M+H⁺, 100), 342 (M+3⁺, 39).

Example 10: N¹-[4-(2-methyl)quinazolinyl]-4-hydroxyl-6-methoxy-1,2,3,4-tetrahydroquinoline (Compound 11)

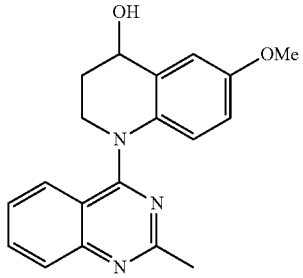 [SMILES: COc1ccc2c(c1)C(O)CCN2c1nc(C)nc2ccccc12]

1-(2-Methylquinazolin-4-yl)-6-methoxy-2,3-dihydroquinolin-4(1H)-one (100 mg, 0.31 mmol) was dissolved in 6 ml methanol, cooled to 0° C., then added with sodium borohydride (23 mg, 0.62 mmol), then heated to room temperature and reacted for 1 h. 0.5 ml of 1N hydrochloric acid was added to the reactants, methanol was removed under vacuum, 20 ml of DCM was added, washed with saturated brine, dried with anhydrous sodium sulfate. The crude product was separated with Flash column chromatography (AcOEt (containing 5% of methanol)/PE=0-2), to obtain Compound 11, which was yellow solid, 62 mg, yield 62%, melting point: 76-78° C. ¹H NMR (CDCl₃): δ ppm 2.13 (1H, m, 3'-CH), 2.37 (1H, m, 3'-CH), 2.74 (3H, s, CH₃), 3.82 (3H, s, OCH₃), 4.00 (1H, m, 2'-CH), 4.21 (1H, m, 2'-CH), 4.94 (1H, m, 4'-CH), 6.60 (1H, dd, $J$=9.2 Hz and 2.8 Hz, ArH-7'), 6.66 (1H, d, $J$=9.2 Hz, ArH-8'), 7.06 (1H, s, $J$=2.8 Hz, ArH-5'), 7.19 (1H, m, ArH-6), 7.50 (1H, d, $J$=8.4 Hz, ArH-5), 7.67 (1H, m, ArH-7), 7.84 (1H, d, $J$=8.4 Hz, ArH-8). LCMS-ESI m/z (%): 322 (M+H⁺, 100).

Example 11: N¹-[4-(2-chloro)quinazolinyl]-4-ethoxy-6-methoxy-1,2,3,4-tetrahydroquinoline (Method I, Compound 12)

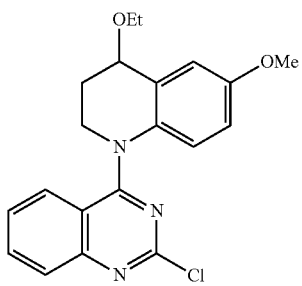 [SMILES: CCOC1CCN(c2nc(Cl)nc3ccccc23)c2ccc(OC)cc21]

Compound 12 was obtained after reaction under refluxing for 2 h, which was yellow solid, 264 mg, yield 78%, melting point 70-72° C. ¹H NMR (CDCl₃): δ ppm 1.27 (3H, t, $J$=6.8 Hz, CH₃), 2.18 (1H, m, 3'-CH), 2.33 (1H, m, 3'-CH), 3.67 (1H, m, 2'-CH), 3.75 (1H, m, 2'-CH), 3.84 (3H, s, OCH₃), 4.12 (2H, m, OCH₂), 4.54 (1H, t, $J$=6.0 Hz, 4'-CH), 6.63 (1H, dd, $J$=9.2 Hz and 2.8 Hz, ArH-7'), 6.72 (1H, d, $J$=8.8 Hz, ArH-8'), 7.03 (1H, d, $J$=2.8 Hz, ArH-5'), 7.14 (1H, m, ArH-6), 7.34 (1H, d, $J$=8.4 Hz, ArH-5), 7.65 (1H, m, ArH-7), 7.80 (1H, d, $J$=8.4 Hz, ArH-8). MS m/z (%) 370 (M+H⁺, 100), 372 (M+3⁺, 43).

Example 12: N⁴-[4-(2-chloro)quinazolinyl]-7-methoxy-3,4-dihydro-2H-benzo[b][1,4]oxazine (Method I, Compound 13)

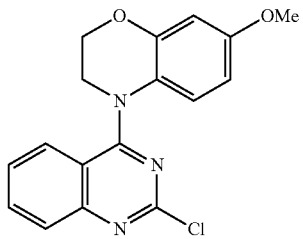 [SMILES: COc1ccc2c(c1)OCCN2c1nc(Cl)nc2ccccc12]

Compound 13 was obtained after reaction under refluxing for 1 h, which was yellow solid, 176 mg, yield 54%, melting point 173-174° C. ¹H NMR (CDCl₃): δ ppm 3.79 (3H, s, 7-OCH₃), 4.23 (2H, t, $J$=4.8 Hz, 3-CH₂), 4.51 (2H, t, $J$=4.8 Hz, 2-CH₂), 6.31 (1H, dd, $J$=8.8 Hz and 2.8 Hz, ArH-6), 6.54 (1H, d, $J$=2.8 Hz, ArH-8), 6.72 (1H, d, $J$=8.8 Hz, ArH-5), 7.29 (1H, m, ArH-6'), 7.73 (1H, m, ArH-7'), 7.81 (1H, d, $J$=8.4 Hz, ArH-5'), 7.84 (1H, d, $J$=8.4 Hz, ArH-8'). MS m/z (%) 328 (M+H⁺, 100), 330 (M+3⁺, 50).

Example 13: N⁴-[4-(2-methyl)quinazolinyl]-6-fluoro-7-methoxy-3,4-dihydro-2H-benzo[b][1,4]oxazine (Method II, Compound 14)

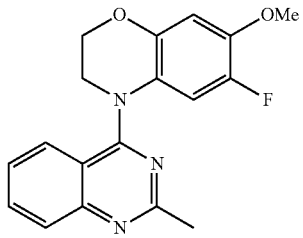 [SMILES: COc1cc2c(cc1F)N(c1nc(C)nc3ccccc13)CCO2]

Compound 14 was obtained after reaction under refluxing for 1 h, which was yellow solid, 132 mg, yield 81%, melting point 192-194° C.; ¹H NMR (CDCl₃): δ ppm 2.74 (3H, s, 2'-CH₃), 3.86 (3H, s, 7-OCH₃), 4.14 (2H, t, $J$=4.8 Hz, 3-CH₂), 4.45 (2H, t, $J$=5.2 Hz, 2-CH₂), 6.55 (1H, d, $J$=12.8 Hz, ArH-5), 6.59 (1H, d, $J$=8.4 Hz, ArH-8), 7.35 (1H, m, ArH-6'), 7.74 (1H, m, ArH-7'), 7.83 (1H, dd, $J$=8.4 Hz and 0.8 Hz, ArH-5'), 7.88 (1H, d, $J$=8.4 Hz, ArH-8'). MS m/i (%) 326 (M+H⁺, 100).

Example 14: N¹-[4-(2-chloro)quinazolinyl]-6-methoxy-2,3-dihydroquinolin-4(1H)-one (Method II, Compound 18)

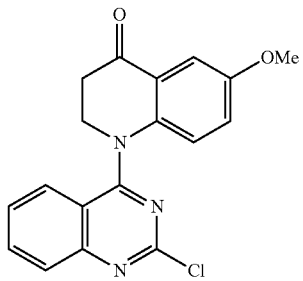 [SMILES: COc1ccc2c(c1)C(=O)CCN2c1nc(Cl)nc2ccccc12]

Compound 18 was obtained after reaction at room temperature overnight, which was yellow solid, 122 mg, yield 36%, melting point 218-220° C. ¹H NMR (CDCl₃): δ ppm 2.98 (2H, t, $J$=6.4 Hz, 3'-CH₂), 3.87 (3H, s, 6'-OCH₃), 4.51

(2H, t, J=6.4 Hz, 2'-CH₂), 6.68 (1H, d, J=9.2 Hz, ArH-8'), 6.88 (1H, dd, J=8.8 Hz and 3.2 Hz, ArH-7'), 7.34 (1H, m, ArH-6), 7.52 (1H, d, J=3.2 Hz, ArH-5'), 7.59 (1H, d, J=8.4 Hz, ArH-5), 7.78 (1H, m, ArH-7), 7.91 (1H, d, J=9.2 Hz, ArH-8). MS m/z (%) 340 (M+H$^+$, 100), 342 (M+3$^+$, 31).

Example 15: N$^4$-[4-(2-methyl)quinazolinyl]-7-methoxy-3,4-dihydroquinoxalin-2(1H)-one (Compound 19)

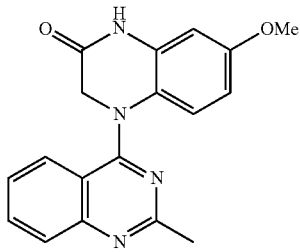 [SMILES: COc1ccc2c(c1)NC(=O)CN2c1nc(C)nc2ccccc12]

This compound was synthesized via 4 steps: 1) 440 mg crude product of 2-methyl-4-(2-nitro-4-methoxy)anilinoquinazoline was prepared according to Method II; 2) the product of step 1) was dissolved in 25 ml of ethyl acetate, 30 mg of Pd/C (10% w/w) was added to perform catalytic hydrogenation reduction at ambient temperature and pressure. The reaction was complete within 2 h, ethyl acetate was removed under vacuum to obtain 320 mg crude product of 2-methyl-4-(2-amino-4-methoxy)anilinoquinazoline; 3) the product of step 2) was dissolved in 15 ml of acetone, chloroacetyl chloride 226 mg (2.0 mmol) and anhydrous potassium carbonate (414 mg, 1.5 mmol) were added, the resulting mixture was reacted under ice-bath for 1 h, the reactants was poured into ice-water, extracted with ethyl acetate (3×30 ml), and the organic phase was washed with saturated brine, dried with anhydrous sodium sulfate, concentrated under vacuum to obtain 364 mg rufous solid crude product of 2-methyl-4-(2-(N-1-oxy-2-chloroethyl)amino-4-methoxy) anilinoquinazoline; 4) the solid of step 3) and anhydrous potassium carbonate (276 mg, 2.0 mmol) were added into 5 ml of DMF, heated to 100° C. and reacted for 2, then the reactant was poured into ice-water, stirred overnight to precipitate orange solid, which was then filtered and dried. The crude product was subjected to Flash column chromatography to obtain Compound 19, which was yellow solid, 122 mg; total yield 38%, melting point 232-233° C. $^1$H NMR (CDCl₃): δ ppm 2.78 (3H, s, 2'-CH₃), 3.81 (3H, s, 7-OCH₃), 4.68 (2H, s, 3-CH₂), 6.40 (1H, dd, J=9.2 Hz and 2.8 Hz, ArH-6), 6.57 (1H, d, J=2.8 Hz, ArH-8), 6.62 (1H, d, J=8.8 Hz, ArH-5), 7.22 (1H, m, ArH-6'), 7.48 (1H, d, J=8.4 Hz, ArH-5'), 7.70 (1H, m, ArH-7'), 7.88 (1H, d, J=8.4 Hz, ArH-8'), 8.63 (1H, brs, 1-NH). MS m/z (%) 321 (M+H$^+$, 100).

Example 16: 6-methoxy-2'-methyl-3,4-dihydro-2H-1,4'-biquinoline (Compound 20)

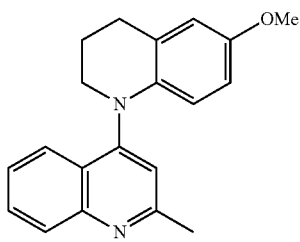 [SMILES: COc1ccc2c(c1)CCCN2c1cc(C)nc2ccccc12]

2-Methyl-4-chloroquinoline (178 mg, 1.0 mmol), 6-methoxy-1,2,3,4-tetrahydro-quinoline (1.2 mmol), palladium acetate (6 mg, 0.03 mmol), X-Phos (17 mg, 0.04 mmol) and Cs₂CO₃ (456 mg, 1.4 mmol) were added into 5 ml of toluene, reacted at 100° C. for 10 h. Insoluble substance was removed by filtration, crude product was separated with silica gel column chromatography to obtain Compound 20, which was yellow solid, 228 mg, yield 75%, melting point 120-121° C. $^1$H NMR (CDCl₃): δ ppm 2.03 (2H, m, 3'-CH₂), 2.65 (3H, s, 2-CH₃), 2.94 (2H, t, J=6.4 Hz, 4'-CH₂), 3.71 (2H, t, J=5.6 Hz, 2'-CH₂), 3.77 (3H, s, 6'-OCH₃), 6.46 (1H, d, J=9.2 Hz, ArH-8'), 6.53 (1H, dd, J=9.2 Hz and 2.8 Hz, ArH-7'), 6.71 (1H, d, J=2.8 Hz, ArH-5'), 6.97 (1H, s, ArH-3), 7.38 (1H, m, ArH-6), 7.64 (1H, m, ArH-7), 7.90 (1H, d, J=8.4 Hz, ArH-8), 8.01 (1H, d, J=8.4 Hz, ArH-5). MS m/z (%) 305 (M+H$^+$, 100).

Example 17: N$^1$-[(3-bromo-5-methoxycarbonyl)phenyl]-6-methoxy-1,2,3,4-tetrahydroquinoline (Compound 26)

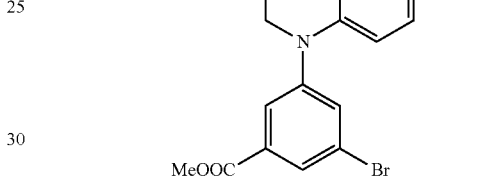

Methyl 3,5-dibromobenzoate (294 mg, 1.0 mmol), 6-methoxy-1,2,3,4-tetrahydroquinoline (179 mg, 1.1 mmol), BINAP (31 mg, 0.05 mmol) and palladium acetate (10 mg, 0.05 mmol) were added to 8 ml of toluene, Cs₂CO₃ (456 mg, 1.4 mmol) was added under nitrogen gas, heated to 100° C. and reacted for 12 h. A small amount of ethyl acetate was added, insoluble substance was removed by filtration, and the crude product was separated with silica gel column chromatography to obtain Compound 26, which was yellow oil, 255 mg, yield 77%. $^1$H NMR (CDCl₃): δ ppm 1.96 (2H, m, 3'-CH₂), 2.76 (2H, t, J=6.4 Hz, 4'-CH₂), 3.61 (2H, t, J=6.0 Hz, 2'-CH₂), 3.78 (3H, s, OCH₃), 3.89 (3H, s, OCH₃), 6.65 (1H, dd, J=8.8 Hz and 3.2 Hz, ArH-7'), 6.68 (1H, d, J=2.8 Hz, ArH-5'), 6.95 (1H, d, J=9.2 Hz, ArH-8'), 7.43 (1H, t, J=2.0 Hz, ArH-4), 7.66 (1H, t, J=2.0 Hz and 1.6 Hz, ArH-6), 7.66 (1H, dd, J=1.2 Hz and 0.8 Hz, ArH-2). MS m/z (%) 376 (M+H$^+$, 100), 378 (M+3$^+$, 91).

Example 18: N$^1$-[(3-bromo-5-carboxyl)phenyl]-6-methoxy-1,2,3,4-tetrahydro-quinoline (Compound 27)

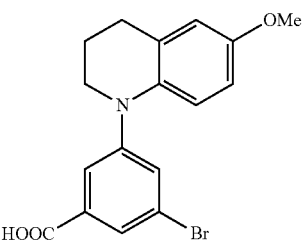 [SMILES: COc1ccc2c(c1)CCCN2c1cc(Br)cc(C(=O)O)c1]

Methyl 3-bromo-5-(6-methoxy-3,4-dihydroquinolin-1(2H)-yl)benzoate (226 mg, 0.6 mmol) was dissolved in a mixed solution of methanol and tetrahydrofuran (2.5 ml/2.5 ml), added with 3N sodium hydroxide solution, stirred at room temperature for 24 h. Then, the reactant was poured into ice water, insoluble was removed by filtration, and the pH of the filtrate was adjusted with 2N hydrochloric acid until no precipitate was separated out. The precipitation was collected by filtration, dried to give Compound 27, which was yellow solid, 178 mg, yield 82%, melting point 175-177° C. $^1$H NMR (CDCl$_3$): δ ppm 1.97 (2H, m, 3'-CH$_2$), 2.76 (2H, t, J=6.4 Hz, 4'-CH$_2$), 3.62 (2H, t, J=6.0 Hz, 2'-CH$_2$), 3.79 (3H, s, OCH$_3$), 6.69 (2H, m, ArH-5' and 7'), 6.98 (1H, d, J=8.8 Hz, ArH-8'), 7.48 (1H, t, J=2.0 Hz, ArH-4), 7.70 (1H, t, J=1.6 Hz and 1.2 Hz, ArH-6), 7.66 (1H, t, J=2.0 Hz and 1.6 Hz, ArH-2). MS m/z (%) 362 (M+H$^+$, 100), 364 (M+3$^+$, 72).

Example 19: N$^1$-[(3-bromo-5-methylaminoacyl) phenyl]-6-methoxy-1,2,3,4-tetrahydroquinoline (Compound 28)

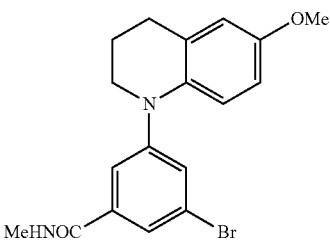

Methyl 3-bromo-5-(6-methoxy-3,4-dihydroquinolin-1 (2H)-yl)benzoate (64 mg, 0.17 mmol) and 25-30% methylamine methanol solution (3 ml) in a sealed tube were heated to 100° C. under microwaves and reacted for 30 minutes. After the completion of the reaction, the reactant was poured into about 20 ml of ice-water, adjusted pH with 2N hydrochloric acid to neutral, extracted with AcOEt (3×20 ml), washed with saturated brine, dried with anhydrous sodium sulfate, and the crude product was separated by column chromatography to obtain Compound 28, which was white solid, 57 mg, yield 90%, melting point: 166-167° C. $^1$H NMR (CDCl$_3$): δ ppm 1.96 (2H, m, 3'-CH$_2$), 2.75 (2H, t, J=6.0 Hz, 4'-CH$_2$), 2.99 (3H, d, J=4.8 Hz, NHCH$_3$), 3.60 (2H, t, J=6.0 Hz, 2'-CH$_2$), 3.78 (3H, s, OCH$_3$), 6.02 (1H, bs, NH), 6.68 (2H, m, ArH-5' and 7'), 6.96 (1H, d, J=8.4 Hz, ArH-8'), 7.32 (1H, s, ArH-4), 7.36 (1H, s, ArH-6), 7.44 (1H, s, ArH-2). MS m/z (%) 375 (M+H$^+$, 100), 377 (M+3$^+$, 97).

Example 20: N$^1$-[3-bromo-5-(N-cyclopropylaminoacyl)phenyl]-6-methoxy-1,2,3,4-tetrahydroquinoline (Compound 29)

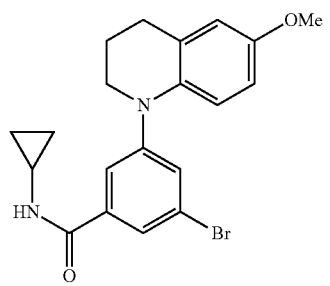 [SMILES: COc1ccc2c(c1)CCCN2c1cc(Br)cc(C(=O)NC2CC2)c1]

3-Bromo-5-(6-methoxy-3,4-dihydroquinolin-1(2H)-yl) benzoic acid (109 mg, 0.3 mmol) was dissolved in dichloromethane (5 ml), added with HOBt (81 mg, 0.6 mmol) and EDCI (115 mg, 0.6 mmol), stirred at room temperature for 30 minutes. Then cyclopropylamine (56 mg, 1.0 mmol) was added, and the reaction was continued for 24 h. The reactant was poured into about 30 ml of ice-water, extracted with AcOEt (3×30 ml), washed with saturated brine, dried with anhydrous sodium sulfate, and the crude product was separated by column chromatography, to obtain Compound 29, which was white solid, 108 mg, yield 90%, melting point 164-166° C. $^1$H NMR (CDCl$_3$): δ ppm 0.61 (2H, m, CH$_2$), 0.86 (2H, m, CH$_2$), 1.95 (2H, m, 3'-CH$_2$), 2.75 (2H, t, J=6.4 Hz, 4'-CH$_2$), 2.86 (1H, m, CH), 3.60 (2H, t, J=6.0 Hz, 2'-CH$_2$), 3.78 (3H, s, OCH$_3$), 6.12 (1H, bs, NH), 6.66 (2H, m, ArH-5' and 7'), 6.95 (1H, d, J=8.4 Hz, ArH-8'), 7.26 (1H, m, ArH-4), 7.35 (1H, m, ArH-6), 7.43 (1H, m, ArH-2). MS m/z (%) 401 (M+H$^+$, 100), 403 (M+3$^+$, 90).

Example 21: N$^1$-[4-(2-amino-6-chloro)pyrimidinyl]-6-methoxy-1,2,3,4-tetrahydro-quinoline (Compound 30)

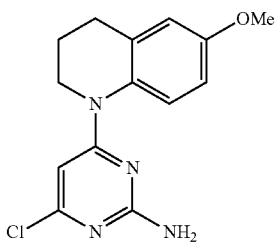 [SMILES: COc1ccc2c(c1)CCCN2c1cc(Cl)nc(N)n1]

A mixture of 2-amino-4,6-dichloropyrimidine (1.0 mmol), 6-methoxy-1,2,3,4-tetrahydro-quinoline (1.2 mmol), hydrochloric acid (2 N, 0.75 ml) and ethanol (3.0 ml)/water (6.0 ml) was refluxed for 20 h. Then, the reactant was poured into ice water, added dropwise with saturated NaHCO$_3$ solution until no precipitate was separated out, filtrated, and dried. Silica gel column chromatography was used for separation to obtain Compound 30, which was white solid, 145 mg, yield 50%, melting point 179-181° C. $^1$H NMR (CDCl$_3$): δ ppm 1.94 (2H, m, 3'-CH$_2$), 2.72 (2H, t, J=6.8 Hz, 4'-CH$_2$), 3.81 (3H, s, OCH$_3$), 3.89 (2H, t, J=6.8 Hz, 2'-CH$_2$), 4.89 (2H, brs, NH$_2$), 6.32 (1H, s, ArH-5), 6.72 (1H, d, J=2.8 Hz, ArH-5'), 6.75 (1H, dd, J=8.4 Hz and 2.8 Hz, ArH-7'), 7.24 (1H, d, J=8.4 Hz, ArH-8'). MS m/z (%) 291 (M+H$^+$, 100), 293 (M+3$^+$, 40).

Example 22: N$^1$-methyl-N$^4$-[4-(2-methyl)quinazolinyl]-7-methoxy-3,4-dihydro-quinoxalin-2(1H)-one (Compound 31)

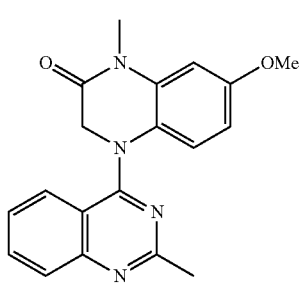 [SMILES: COc1ccc2c(c1)N(C)C(=O)CN2c1nc(C)nc2ccccc12]

Compound 19 (60 mg, 0.19 mmol) was dissolved in 3 ml of DMF, cooled with ice-bath to 0° C., added successively with iodomethane (0.02 ml, 0.32 mmol) and sodium hydride (16 mg, 0.4 mmol), and reacted for 1 h. The reactant was poured into ice-water, solid substance was precipitated, filtered, and dried. The crude product was separated with Flash column chromatography to obtain Compound 31, which was yellow solid, 53 mg; yield 84%, melting point 217-218° C. $^1$H NMR (CDCl$_3$): δ ppm 2.77 (3H, s, CH$_3$), 3.48 (3H, s, NCH$_3$), 3.83 (3H, s, OCH$_3$), 4.67 (2H, s, CH$_2$), 6.41 (1H, dd, J=9.2 Hz and 2.8 Hz, ArH-7'), 6.64 (1H, d, J=8.8 Hz, ArH-5'), 6.72 (1H, d, J=2.8 Hz, ArH-8'), 7.20 (1H, m, ArH-7), 7.47 (1H, d, J=8.4 Hz, ArH-5), 7.69 (1H, m, ArH-6), 7.87 (1H, d, J=8.4 Hz, ArH-8'). MS m/z (%) 335 (M+H$^+$, 100).

Example 23: 2-(N-methylmethylamino)-4-(6-methoxy-1,2,3,4-tetrahydro-1-quinolyl)quinazoline (Compound 32)

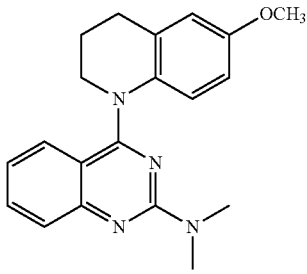 [SMILES: COc1ccc2c(c1)CCCN2c1nc(N(C)C)nc2ccccc12]

Compound 1 (50 mg, 0.15 mmol) in 2 mL of DMF was stirred for 15 minutes in the presence of 0.1 mL of ammonia solution in microwave reaction apparatus at 150° C., leave the reaction tube to cool after the end of the reaction, and the reaction liquid was poured into 20 mL of ice-water to generate yellow precipitate, which was filtered, washed with water, and dried. The crude product was purified with Flash column (methanol/dichloromethane: 0-5%) to obtain 45 mg of the target Compound 32, yield: 88.2%, amber solid. mp 89~91° C.; $^1$H NMR (CDCl$_3$): δ ppm 2.08 (2H, m, 3'-CH$_2$), 2.85 (2H, t, J=6.6 Hz, 4'-CH$_2$), 3.27 (6H, s, 2×NCH$_3$), 3.78 (3H, s, OCH$_3$), 3.97 (2H, t, J=6.7 Hz, 2'-CH$_2$), 6.53 (1H, dd, J=9.0 Hz and 2.8 Hz, ArH-7'), 6.65 (1H, d, J=8.7 Hz, ArH-8'), 6.77 (2H, m, ArH-5' and ArH-6), 7.23 (1H, d, J=8.1 Hz ArH-5), 7.42 (1H, m, ArH-7), 7.50 (1H, d, J=8.1 Hz ArH-8). MS m/z (%): 335 (M+1, 100), 336 (M+3, 18).

Example 24: 2-cyclopropylamino-4-(6-methoxy-1,2,3,4-tetrahydro-1-quinolyl) quinazoline (Compound 33)

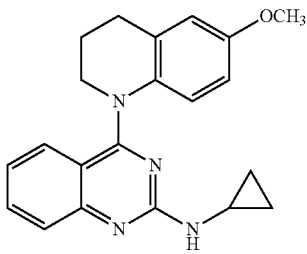 [SMILES: COc1ccc2c(c1)CCCN2c1nc(NC2CC2)nc2ccccc12]

Compound 1 (50 mg, 0.15 mmol), cyclopropylamine (0.1 mL, excessive) and hexanol (2.5 mL) were reacted in microwave reaction apparatus at 150° C. for 15 minutes to obtain 51 mg of target Compound 33, yield: 96.9%, yellow solid, mp 173~175° C.; $^1$H NMR (DMSO-d$_6$) δ ppm 0.51 (2H, m, CH$_2$), 0.66 (2H, m, CH$_2$), 1.97 (2H, m, 3'-CH$_2$), 2.81 (3H, m, 4'-CH$_2$ and CH), 3.71 (3H, s, OCH$_3$), 3.82 (2H, t, J=6.5 Hz, 2'-CH$_2$), 6.56 (1H, dd, J=9.0 Hz and 2.8 Hz, ArH-7'), 6.68 (1H, d, J=9.0 Hz, ArH-8'), 6.76 (1H, d, J=2.8 Hz, ArH-5'), 6.84 (1H, m, ArH-6), 7.29 (1H, d, J=9.1 Hz ArH-5), 7.45 (1H, m, ArH-7), 7.54 (1H, d, J=8.4 Hz ArH-8). MS m/z (%): 347 (M+1, 100).

Example 25: 2-cyclopentylamino-4-(6-methoxy-1,2,3,4-tetrahydro-1-quinolyl) quinazoline (Compound 34)

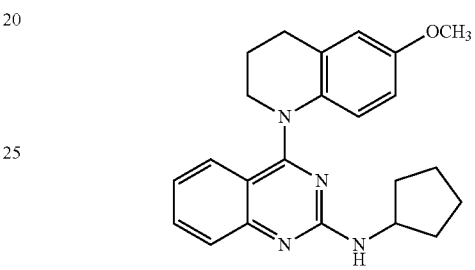

Compound 1 (150 mg, 0.45 mmol), cyclopentylamine (0.1 mL, excess) and hexanol (2.5 mL) were reacted in microwave reaction apparatus at 150° C. for 15 minutes to obtain 138 mg of target Compound 34, yield: 80.1%, yellow solid, mp 178~180° C.; $^1$H NMR (DMSO-d$_6$) δ ppm 1.54 (4H, m, 2×CH$_2$), 1.68 (2H, m, CH$_2$), 1.92 (2H, m, CH$_2$), 1.98 (2H, m, 3'-CH$_2$), 2.81 (2H, t, J=6.9 Hz, 4'-CH$_2$), 3.71 (3H, s, OCH$_3$), 3.82 (2H, t, J=5.6 Hz, 2'-CH$_2$), 4.28 (1H, m, CH), 6.55 (1H, dd, J=8.7 Hz and 2.8 Hz, ArH-7'), 6.68 (1H, d, J=9.0 Hz, ArH-8'), 6.78 (1H, d, J=2.8 Hz, ArH-5'), 6.88 (1H, m, ArH-6), 7.24 (1H, d, J=9.1 Hz ArH-5), 7.45 (1H, m, ArH-7), 7.54 (1H, d, J=8.4 Hz ArH-8). MS m/z (%): 375 (M+1, 100).

Example 26: 2-(3-hydroxylpropylamino)-4-(6-methoxy-1,2,3,4-tetrahydro-1-quinolyl)quinazoline (Compound 35)

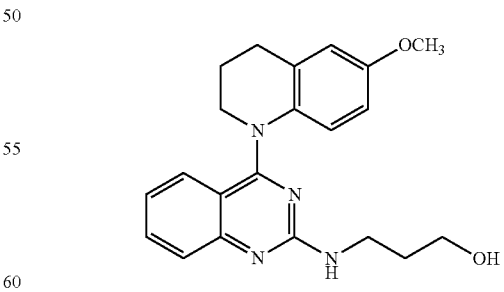

Compound 1 (145 mg, 0.44 mmol), 3-hydroxylpropylamine (0.1 mL, excess) and hexanol (2.5 mL) were reacted in microwave reaction apparatus at 150° C. for 15 minutes to obtain 137 mg of target Compound 35, yield: 71.2%, yellow solid, mp 134~136° C.; $^1$H NMR (CDCl$_3$): a ppm 1.77 (2H, f, J=7.2 Hz, CH$_2$), 2.07 (2H, m, 3'-CH$_2$), 2.85 (2H, t, J=6.8

Hz, 4'-CH$_2$), 3.67 (4H, m, 2CH$_2$), 3.79 (3H, s, OCH$_3$), 3.93 (2H, t, J=6.8 Hz, 2'-CH$_2$), 6.56 (1H, dd, J=8.7 Hz and 2.8 Hz, ArH-7'), 6.70 (1H, d, J=9.0 Hz, ArH-8'), 6.77 (1H, d, J=2.8 Hz, ArH-5'), 6.84 (1H, m, ArH-6), 7.25 (1H, d, J=8.1 Hz ArH-5), 7.47 (2H, m, ArH-7 和 ArH-8), MS m/z (%): 365 (M+1, 100), 366 (M+3, 17).

Example 27: 4-(6-methoxy-1,2,3,4-tetrahydro-1-quinolyl)quinazoline (Compound 36)

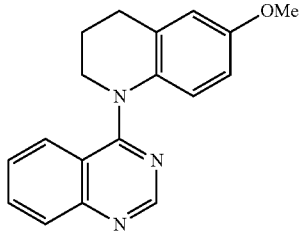 [SMILES: COc1ccc2c(c1)CCCN2c1ncnc2ccccc12]

4-Chloroquinazoline (170 mg, 1.04 mmol) and 6-methoxy-1,2,3,4-tetrahydroquinoline (180 mg, 1.10 mmol) were added into i-PrOH (15 ml), 1 drop of concentrated hydrochloric acid was added, and the resulting mixture was reacted under refluxing for 1 hour to obtain 193 mg of target Compound 36, yield 64.9%, yellow solid. mp 94~95° C.; $^1$H NMR (CDCl$_3$): a ppm 2.11 (2H, f, J=6.4 Hz, 3'-CH$_2$), 2.87 (2H, t, J=6.8 Hz, 4'-CH$_2$), 3.80 (3H, s, OCH$_3$), 4.05 (2H, t, J=6.4 Hz, 2'-CH$_2$), 6.56 (1H, dd, J=8.4 and 2.8 Hz, ArH-7'), 6.65 (1H, d, J=8.8 Hz, ArH-8'), 6.79 (4H, d, J=2.8 Hz, ArH-5'), 7.21 (1H, td, J=8.8 and 1.2 Hz, ArH-6), 7.49 (1H, d, J=8.4 Hz, ArH-5), 7.68 (1H, td, J=8.8 and 2.0 Hz, ArH-7), 7.89 (1H, d, J=8.4 Hz, ArH-8), 8.86 (1H, s, ArH-2). MS m/z (%): 292(M+1, 100).

Example 28: 4-(6-methoxy-1,2,3,4-tetrahydro-1-quinolyl)naphthalene (Compound 37)

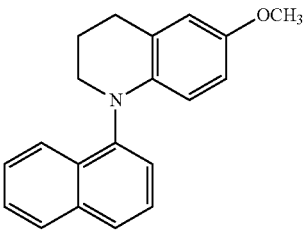 [SMILES: COc1ccc2c(c1)CCCN2c1cccc2ccccc12]

1-Bromo-naphthalene (207 mg, 1.0 mmol) and 6-methoxy-1,2,3,4-tetrahydroquinoline (180 mg, 1.1 mmol) were reacted in toluene (15.0 mL) in the presence of Cs$_2$CO$_3$ (2 equiv), X-Phos (0.05 equiv), and Pd(OAc)$_2$ (0.04 equiv) under refluxing for 3 h to obtain 196 mg of Compound 37, yield 68.6%, grey solid. mp 94~96° C.; $^1$H NMR (CDCl$_3$): δ ppm 2.15 (2H, brs, 3-CH$_2$), 2.98 (2H, brs, 4-CH$_2$), 3.63 (2H, t, J=5.6 Hz, 2-CH$_2$), 3.72 (3H, s, 6-OCH$_3$), 6.06 (1H, d, J=8.8 Hz, ArH-8), 6.41 (1H, dd, J=8.8 Hz and 2.8 Hz, ArH-7), 6.68 (1H, d, J=2.8 Hz, ArH-5), 6.97 (1H, d, J=7.2 Hz, ArH-2'), 7.46 (3H, m, ArH-3', 6' and 7'), 7.74 (1H, d, J=8.0 Hz, ArH-4'), 7.89 (1H, d, J=8.0 Hz, ArH-5'), 8.02 (1H, d, J=8.0 Hz, ArH-8'). MS m/z (%): 274 (M–15$^+$, 100), 290 (M+H$^+$, 100).

Example 29: 4-(6-methoxy-1,2,3,4-tetrahydro-1-quinolyl)quinoline (Compound 38)

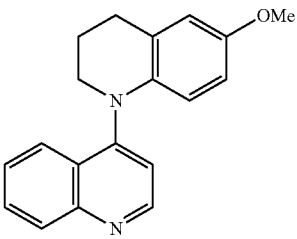 [SMILES: COc1ccc2c(c1)CCCN2c1ccnc2ccccc12]

4-Chloroquinzole (150 mg, 0.92 mmol) and 6-methoxy-1,2,3,4-tetrahydroquinoline (165 mg, 1.01 mmol) were reacted in toluene (15.0 mL) in the presence of Cs$_2$CO$_3$ (2 equiv), X-Phos (0.05 equiv), and Pd(OAc)$_2$ (0.04 equiv) under refluxing for 14 h to obtain 188 mg of target Compound 38, yield 71.2%, yellow solid. mp 41~43° C.; $^1$H NMR (CDCl$_3$): δ ppm 2.11 (2H, f, J=5.2 Hz, 3'-CH$_2$), 2.87 (2H, t, J=6.4 Hz, 4'-CH$_2$), 3.74 (2H, t, J=5.6 Hz, 2'-CH$_2$), 3.77 (3H, s, OCH$_3$), 6.50 (1H, d, J=8.8 Hz, ArH-8'), 6.53 (1H, dd, J=8.8 and 2.4 Hz, ArH-7'), 6.72 (4H, d, J=2.4 Hz, ArH-5'), 7.07 (1H, d J=8.0 Hz, ArH-3), 7.44 (1H, td, J=8.0 and 1.2 Hz, ArH-6), 7.68 (1H, td, J=8.0 and 1.2 Hz, ArH-7), 7.95 (1H, d, J=8.4 Hz, ArH-5), 8.11 (1H, d, J=8.4 Hz, ArH-8), 8.75 (1H, d J=8.0 Hz, ArH-2). MS m/z (%): 291(M+1, 100).

Example 30: 1-(6-methoxy-1,2,3,4-tetrahydro-1-quinolyl)isoquinoline (Compound (Compound 39)

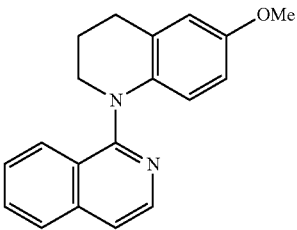 [SMILES: COc1ccc2c(c1)CCCN2c1nccc2ccccc12]

1-Bromoisoquinzole (170 mg, 0.83 mmol) and 6-methoxy-1,2,3,4-tetrahydroquinoline (150 mg, 0.92 mmol) were reacted in toluene (15.0 mL) in the presence of Cs$_2$CO$_3$ (2 equiv), X-Phos (0.05 equiv), and Pd(OAc)$_2$ (0.04 equiv) under refluxing for 26 h to obtain 180 mg of target Compound 39, yield 75.2%, yellow solid. mp 121~122° C.; $^1$H NMR (CDCl$_3$): S ppm 2.12 (2H, f, J=6.0 Hz, 3'-CH$_2$), 2.95 (2H, t, J=6.0 Hz, 4'-CH$_2$), 3.74 (3H, s, OCH$_3$), 3.86 (2H, t, J=5.6 Hz, 2'-CH$_2$), 6.33 (1H, d, J=8.8 Hz, ArH-8'), 6.45 (1H, dd, J=8.8 and 2.0 Hz, ArH-7'), 6.70 (4H, d, J=1.2 Hz, ArH-5'), 6.99 (1H, d, J=8.0 Hz, ArH-4), 7.40 (1H, t, J=8.0 Hz, ArH-7), 7.61 (1H, t, J=8.4 Hz, ArH-6), 7.78 (1H, d, J=8.0 Hz, ArH-5), 7.93 (1H, d, J=8.0 Hz, ArH-8), 8.28 (1H, s, ArH-3). MS m/z (%): 291 (M+1, 100).

Example 31: 4-(6-methoxy-1,2,3,4-tetrahydro-1-quinolyl)isoquinoline (Compound (Compound 40)

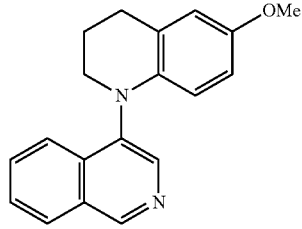 [SMILES: COc1ccc2c(c1)CCCN2c1cncc2ccccc12]

4-Bromoisoquinzole (170 mg, 0.83 mmol) and 6-methoxy-1,2,3,4-tetrahydroquinoline (150 mg, 0.92 mmol) were reacted in toluene (15.0 mL) in the presence of $Cs_2CO_3$ (2 equiv), X-Phos (0.05 equiv), and $Pd(OAc)_2$ (0.04 equiv) under refluxing for 14 h to obtain 180 mg of target Compound 40, yield 75.5%, yellow solid. mp 86~88° C.; $^1$H NMR ($CDCl_3$): δ ppm 2.11 (2H, f, J=5.6 Hz, 3'-$CH_2$), 2.87 (2H, t, J=5.6 Hz, 4'-$CH_2$), 3.74 (2H, t, J=5.2 Hz, 2'-$CH_2$), 3.73 (3H, s, $OCH_3$), 6.13 (1H, d, J=8.8 Hz, ArH-8'), 6.53 (1H, dd, J=8.8 and 2.8 Hz, ArH-7'), 6.70 (4H, d, J=2.8 Hz, ArH-5'), 7.65 (1H, td, J=8.0 and 2.0 Hz, ArH-7), 7.67 (1H, td, J=8.0 and 1.6 Hz, ArH-6), 7.95 (1H, dd, J=8.4 and 2.0 Hz, ArH-5), 8.05 (1H, dd, J=8.4 and 2.0 Hz, ArH-8), 8.41 (1H, s ArH-3), 9.15 (1H, s ArH-1). MS m/z (%): 291(M+1, 100).

Example 32: 8-(6-methoxy-1,2,3,4-tetrahydro-1-quinolyl)quinoline (Compound 41)

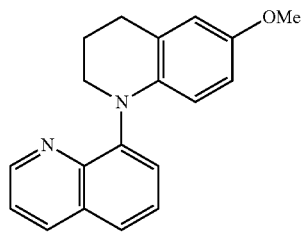 [SMILES: COc1ccc2c(c1)CCCN2c1cccc2cccnc12]

8-Chloroquinzole (550 mg, 3.37 mmol) and 6-methoxy-1,2,3,4-tetrahydroquinoline (570 mg, 3.49 mmol) were reacted in toluene (15.0 mL) in the presence of $Cs_2CO_3$ (2 equiv), X-Phos (0.05 equiv), and $Pd(OAc)_2$ (0.04 equiv) under refluxing for 12 h to obtain 598 mg of target Compound 41, yield 61.3%, yellow solid. mp 86~88° C.; $^1$H NMR ($CDCl_3$): S ppm 2.00 (2H, f, J=5.6 Hz, 3'-$CH_2$), 2.93 (2H, t, J=6.4 Hz, 4'-$CH_2$), 3.74 (3H, s, $OCH_3$), 3.74 (2H, t, J=6.0 Hz, 2'-$CH_2$), 6.49 (1H, d, J=8.0 Hz, ArH-8'), 6.50 (1H, dd, J=8.0 and 0.8 Hz, ArH-7'), 6.65 (4H, d, J=0.8 Hz, ArH-5'), 7.39 (1H, td, J=8.0 and 1.2 Hz, ArH-6), 7.41 (1H, td, J=8.0 and 1.2 Hz, ArH-3), 7.45 (1H, dd, J=8.0 and 2.0 Hz, ArH-5), 7.56 (1H, dd, J=8.0 and 2.0 Hz, ArH-4), 8.15 (1H, dd, J=8.0 and 2.0 Hz, ArH-7), 8.75 (1H, d, J=7.6 Hz, ArH-2). MS m/z (%): 291(M+1, 100).

Example 33: 6-(6-methoxy-1,2,3,4-tetrahydro-1-quinolyl)purine (Compound 42)

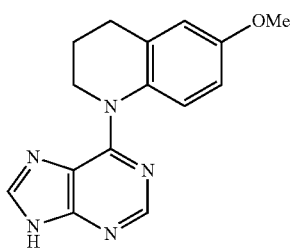 [SMILES: COc1ccc2c(c1)CCCN2c1ncnc2[nH]cnc12]

6-Chloropurine (150 mg, 0.97 mmol) and 6-methoxy-1,2,3,4-tetrahydroquinoline (180 mg, 1.10 mmol) were added into i-PrOH (15 ml), 1 drop of concentrated hydrochloric acid was added, and the resulting mixture was reacted under refluxing for 5 h to obtain 201 mg of target Compound 42, yield 73.6%, white solid. mp 189~191° C.; $^1$H NMR ($CDCl_3$): δ ppm 2.10 (2H, m, 3'-$CH_2$), 2.87 (2H, t, J=6.4 Hz, 4'-$CH_2$), 3.82 (3H, s, $OCH_3$), 4.59 (2H, t, J=6.4 Hz, 2'-$CH_2$), 6.73 (1H, d, J=2.0 Hz, ArH-5'), 6.77 (1H, dd, J=8.8 and 2.4 Hz, ArH-7'), 7.52 (1H, d, J=8.8 Hz, ArH-8'), 8.03 (1H, s, ArH-8), 8.48 (1H, s, ArH-2). MS m/z (%): 282(M+1, 100), 283 (M+2.8).

Example 34: 2-fluoro-6-(6-methoxy-1,2,3,4-tetrahydro-1-quinolyl)purine (Compound 43)

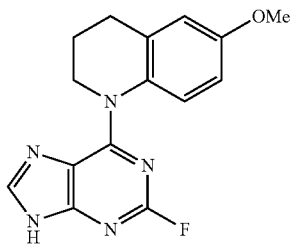 [SMILES: COc1ccc2c(c1)CCCN2c1nc(F)nc2[nH]cnc12]

6-Chloro-2-fluoropurine (110 mg, 0.64 mmol) and 6-methoxy-1,2,3,4-tetrahydroquinoline (115 mg, 0.70 mmol) were added into i-PrOH (15 ml), 1 drop of concentrated hydrochloric acid was added, and the resulting mixture was reacted under refluxing for 4 h to obtain 137 mg of target Compound 43, yield 72.6%, white solid. mp 218~220° C.; $^1$H NMR ($CDCl_3$): δ ppm 2.12 (2H, f, J=6.8 Hz, 3'-$CH_2$), 2.86 (2H, t, J=6.8 Hz, 4'-$CH_2$), 3.82 (3H, s, $OCH_3$), 4.56 (2H, t, J=6.8 Hz, 2'-$CH_2$), 6.71 (1H, d, J=2.8 Hz, ArH-5'), 6.77 (1H, dd, J=8.8 and 2.8 Hz, ArH-7'), 7.54 (1H, d, J=8.8 Hz, ArH-8'), 7.93 (1H, s, ArH-8). MS m/z (%): 300 (M+1, 100).

Example 35: 2-amino-6-(6-methoxy-1,2,3,4-tetra-hydro-1-quinolyl)purine (Compound 44)

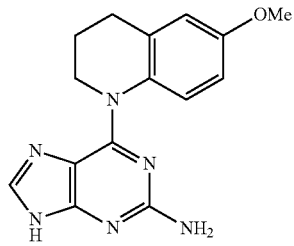 [SMILES: COc1ccc2c(c1)CCCN2c1nc(N)nc2[nH]cnc12]

2-Amino-6-chloropurine (150 mg, 0.89 mmol) and 6-methoxy-1,2,3,4-tetrahydroquinoline (160 mg, 0.98 mmol) were added into i-PrOH (15 ml), 1 drop of concentrated hydrochloric acid was added, and the resulting mixture was reacted under refluxing for 4.5 h to obtain 157 mg of target Compound 44, yield 60.6%, white solid. mp 183~186° C.; $^1$H NMR (DMSO-$d_6$) δ ppm 0.83 (2H, m, 3'-CH$_2$), 1.97 (2H, t, J=6.0 Hz, 4'-CH$_2$), 2.79 (2H, t, J=6.0 Hz, 2'-CH$_2$), 3.79 (3H, s, OCH$_3$), 6.79 (1H, dd, J=8.4 and 2.4 Hz, ArH-7'), 6.81 (1H, d, J=2.8 Hz, ArH-5'), 7.29 (1H, d, J=8.8 Hz, ArH-8'), 8.11 (1H, s, ArH-8). MS m/z (%): 297 (M+1, 100).

Example 36: Experiments of Inhibiting Growth of Cancer Cells

The human cancer cells (A549, DU145, KB, KB-VIN, etc.) were placed in single medium (RPMI-1640 containing 10% (v/v) fetal bovine serum), and the morphological characteristics and growth conditions of cells in medium were observed with microscope. The cells were placed in 2.5 cm culture dish and cultured at 37° C. in wet air containing 5% $CO_2$. Cell lines grew adhering to wall. The preparation and dilution of samples as well as process for inoculating them to cellular fluid were performed under aseptic condition. The test samples usually were dissolved in DMSO, stored at −70° C. The cultured cells were added to 96-well culture plate, and each well had a cell number of 1500-7500, after culturing for 24 h, the test drugs with different concentrations were added, and stood continuously for 48 h. $GI_{50}$ values about inhibiting growth of cancer cells were determined by SRB (sulfonyl rhodamine B) method. Anticancer drug paclitaxel was used as positive control.

A549: lung cancer cells; DU145: prostate cancer cells; KB: nasopharyngeal cancer cells; KB-VIN: drug-resistant nasopharyngeal cancer cells. $GI_{50}$ value was the concentration that causes 50% cancer cells growth inhibition, showing anticancer activity. Partial test results of anticancer activity of the compounds of the present invention were shown in Table 1.

TABLE 1

Compounds of Formula I of the present invention and data of their anticancer activity

| Compound | $GI_{50}$ (µg/ml) | | | |
|---|---|---|---|---|
| | A549 | DU145 | KB | KB-VIN |
| 1 | 0.0006 | 0.0005 | 0.0006 | 0.0006 |
| 2 | 0.0056 | 0.0046 | 0.0034 | 0.0055 |
| 3 | 0.0077 | 0.0069 | 0.0085 | 0.0096 |
| 4 | 0.0088 | 0.0075 | 0.0080 | 0.0092 |
| 6 | 0.061 | 0.051 | 0.054 | 0.059 |
| 7 | 0.075 | 0.060 | 0.070 | 0.063 |
| 8 | 0.0679 | 0.0590 | 0.0660 | 0.0695 |
| 9 | 5.336 | 4.764 | 6.256 | 4.715 |
| 10 | 0.065 | 0.056 | 0.077 | 0.067 |
| 11 | 0.006 | 0.006 | 0.006 | 0.006 |
| 12 | 0.065 | 0.060 | 0.066 | 0.072 |
| 13 | 0.065 | 0.055 | 0.050 | 0.0639 |
| 14 | 4.705 | 7.772 | 4.568 | 5.769 |
| 18 | 0.0091 | 0.0106 | 0.0661 | 0.0765 |
| 19 | 0.0010 | 0.0007 | 0.0006 | 0.0008 |
| 20 | 0.0138 | 0.0115 | 0.0278 | 0.0168 |
| 26 | 0.421 | 0.483 | 0.517 | 0.476 |
| 28 | 0.140 | 0.209 | 0.237 | 0.349 |
| 29 | 0.067 | 0.062 | 0.066 | 0.076 |
| 30 | 0.077 | 0.060 | 0.070 | 0.070 |
| 31 | 0.0063 | 0.0072 | 0.0056 | 0.0082 |
| 32 | 0.056 | 0.051 | 0.048 | 0.066 |
| 33 | 0.0057 | 0.0045 | 0.0045 | 0.0056 |
| 34 | 0.501 | 0.483 | 0.444 | 0.531 |
| 35 | 0.0058 | 0.0073 | 0.0067 | 0.0070 |
| 37 | 5.153 | 4.271 | 4.519 | 5.114 |
| Paclitaxel | 0.0065 | 0.0053 | 0.0063 | 0.726 |

Notation: A549: lung cancer cells; DU145: prostate cancer cells; KB: nasopharyngeal cancer cells; KB-VIN: drug-resistant nasopharyngeal cancer cells.
The concentration that causes 50% cancer cells growth inhibition ($GI_{50}$) represents anticancer activity.

What is claimed is:

1. A compound of Formula I or a pharmaceutically acceptable salt thereof:

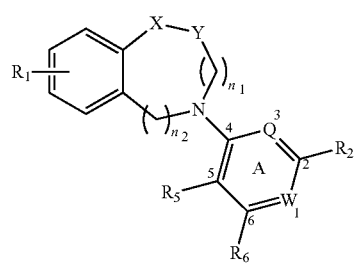

wherein,

X is —NR'—, and Y is —C(O)—, —CHOR'—, or —CR'R"—; wherein R' and R" each independently are H, $C_{1-6}$ alkyl, $C_{1-6}$ alkoxyl, $C_{1-6}$ alkylamino, or hydroxyl;

$R_1$ represents 1 or 2 substituents optionally existing on the benzene ring, independently being $C_{1-6}$ alkyl, $C_{1-6}$ alkoxyl, halogen, hydroxyl, cyano, amino, or $C_{1-6}$ alkylamino;

$R_2$ is $C_{1-6}$ alkyl, $C_{1-6}$ alkoxyl, halogen, acyl, alkenyl, alkynyl, hydroxyl, cyano, alkylamino, dialkylamino, acylamino, alkylthio, cycloalkyl, cyano alkyl, heterocycloalkyl or aryl;

Q and W each independently are N;

$R_5$ and $R_6$ together with carbon atoms linked to them form 6-membered aromatic ring forming a conjugated system, wherein the aromatic ring is optionally substituted with 1 or 2 $R_3$;

$R_3$ independently is H, $C_{1-6}$ alkyl, $C_{1-6}$ alkoxyl, fluorine, chlorine, bromine, iodine, acyl, hydroxyl, cyano, amino, $C_{1-6}$ alkylamino, $C_{1-6}$ dialkylamino, acylamino, $C_{1-6}$ alkylthio, or $C_{3-6}$ cycloalkyl;
$n_1=1$; and
$n_2=0$.

2. A compound selected from the group consisting of:
$N^1$-[4-(2-chloro)quinazolinyl]-6-methoxy-1,2,3,4-tetrahydroquinoline (Compound 1),
$N^1$-[4-(2-methyl)quinazolinyl]-6-methoxy-1,2,3,4-tetrahydroquinoline (Compound 2),
$N^1$-[4-(2-methoxy)quinazolinyl]-6-methoxy-1,2,3,4-tetrahydroquinoline (Compound 3),
$N^1$-[4-(2-methylamino)quinazolinyl]-6-methoxy-1,2,3,4-tetrahydroquinoline (Compound 4),
2-methyl-4-(6-methoxy-7-fluoro-3,4-dihydroquinolin-1(2H)-yl)quinazoline (Compound 5),
$N^1$-[4-(2-methyl)quinazolinyl]-6-methyl-1,2,3,4-tetrahydroquinoline (Compound 6),
$N^1$-[4-(2-methyl)quinazolinyl]-6-bromo-1,2,3,4-tetrahydroquinoline (Compound 7),
$N^2$-[4-(2-methyl)quinazolinyl]-7-methoxy-2,3,4,5-tetrahydro-1H-benzo[c]azepine (Compound 9),
$N^1$-[4-(2-chloro)quinazolinyl]-7-methoxy-2,3,4,5-tetrahydro-1H-benzo[b]azepine (Compound 10),
$N^1$-[4-(2-methyl)quinazolinyl]-4-hydroxyl-6-methoxy-1,2,3,4-tetrahydroquinoline (Compound 11),
$N^1$-[4-(2-chloro)quinazolinyl]-4-ethoxy-6-methoxy-1,2,3,4-tetrahydroquinoline (Compound 12),
$N^4$-[4-(2-chloro)quinazolinyl]-7-methoxy-3,4-dihydro-2H-benzo[b][1,4]oxazine (Compound 13),
$N^4$-[4-(2-methyl)quinazolinyl]-6-fluoro-7-methoxy-3,4-dihydro-2H-benzo[b][1,4]oxazine (Compound 14),
4-(2-chloroquinazolin-4-yl)-7-methoxy-3,4-dihydro-2H-benzo[b][1,4]thiazine (Compound 15),
4-(2-chloroquinazolin-4-yl)-7-methoxy-3,4-dihydro-2H-benzo[b][1,4]-1-oxythiazine (Compound 16),
4-(2-chloroquinazolin-4-yl)-7-methoxy-3,4-dihydro-2H-benzo[b][1,4]-1,1-dioxythiazine (Compound 17),
$N^1$-[4-(2-chloro)quinazolinyl]-6-methoxy-2,3-dihydroquinolin-4(1H)-one (Compound 18),
$N^4$-[4-(2-methyl)quinazolinyl]-7-methoxy-3,4-dihydroquinoxalin-2(1H)-one (Compound 19),
6-methoxy-2'-methyl-3,4-dihydro-2H-1,4'-biquinoline (Compound 20),
2-methyl-4-(6-methoxy-3,4-dihydroquinolin-1(2H)-yl)pyrido[2,3-d]pyrimidine (Compound 21),
2-methyl-4-(6-methoxy-3,4-dihydroquinolin-1(2H)-yl)pyrido[3,4-d]pyrimidine (Compound 22),
2-methyl-4-(6-methoxy-3,4-dihydroquinolin-1(2H)-yl)pyrido[4,3-d]pyrimidine (Compound 23),
2-methyl-4-(6-methoxy-3,4-dihydroquinolin-1(2H)-yl)pyrido[3,2-d]pyrimidine (Compound 24),
2-methyl-4-(6-methoxy-3,4-dihydroquinolin-1(2H)-yl)pteridine (Compound 25),
$N^1$-[(3-bromo-5-methoxycarbonyl)phenyl]-6-methoxy-1,2,3,4-tetrahydroquinoline (Compound 26),
$N^1$-[(3-bromo-5-carboxyl)phenyl]-6-methoxy-1,2,3,4-tetrahydroquinoline (Compound 27),
$N^1$-[(3-bromo-5-methylaminoacyl)phenyl]-6-methoxy-1,2,3,4-tetrahydroquinoline (Compound 28),
$N^1$-[3-bromo-5-(N-cyclopropylaminoacyl)phenyl]-6-methoxy-1,2,3,4-tetrahydroquinoline (Compound 29),
$N^1$-[4-(2-amino-6-chloro)pyrimidinyl]-6-methoxy-1,2,3,4-tetrahydroquinoline (Compound 30),
$N^1$-methyl-$N^4$-[4-(2-methyl)quinazolinyl]-7-methoxy-3,4-dihydroquinoxalin-2(1H)-one (Compound 31),
2-(N-methylmethylamino)-4-(6-methoxy-1,2,3,4-tetrahydro-1-quinolyl)quinazoline (Compound 32),
2-cyclopropylamino-4-(6-methoxy-1,2,3,4-tetrahydro-1-quinolyl)quinazoline (Compound 33),
2-cyclopentylamino-4-(6-methoxy-1,2,3,4-tetrahydro-1-quinolyl)quinazoline (Compound 34),
2-(3-hydroxylpropylamino)-4-(6-methoxy-1,2,3,4-tetrahydro-1-quinolyl)quinazoline (Compound 35),
4-(6-methoxy-1,2,3,4-tetrahydro-1-quinolyl)quinazoline (Compound 36),
4-(6-methoxy-1,2,3,4-tetrahydro-1-quinolyl)naphthalene (Compound 37),
4-(6-methoxy-1,2,3,4-tetrahydro-1-quinolyl)quinoline (Compound 38),
1-(6-methoxy-1,2,3,4-tetrahydro-1-quinolyl)isoquinoline (Compound 39),
4-(6-methoxy-1,2,3,4-tetrahydro-1-quinolyl)isoquinoline (Compound 40),
8-(6-methoxy-1,2,3,4-tetrahydro-1-quinolyl)quinoline (Compound 41),
6-(6-methoxy-1,2,3,4-tetrahydro-1-quinolyl)purine (Compound 42),
2-fluoro-6-(6-methoxy-1,2,3,4-tetrahydro-1-quinolyl)purine (Compound 43), and
2-amino-6-(6-methoxy-1,2,3,4-tetrahydro-1-quinolyl)purine (Compound 44); or
a pharmaceutically acceptable salt thereof.

3. A pharmaceutical composition, comprising the compound according to any one of claims 2 and 1, or a pharmaceutically acceptable salt thereof, and one or more pharmaceutically acceptable carriers or excipients.

4. A method for preparing the compound of claim 1 or a pharmaceutically acceptable salt thereof, the method comprising:
in the presence of an alkali or acid, reacting a substituted halide of Formula III with a substituted amine compound of Formula II in a solvent to afford a compound of Formula I,

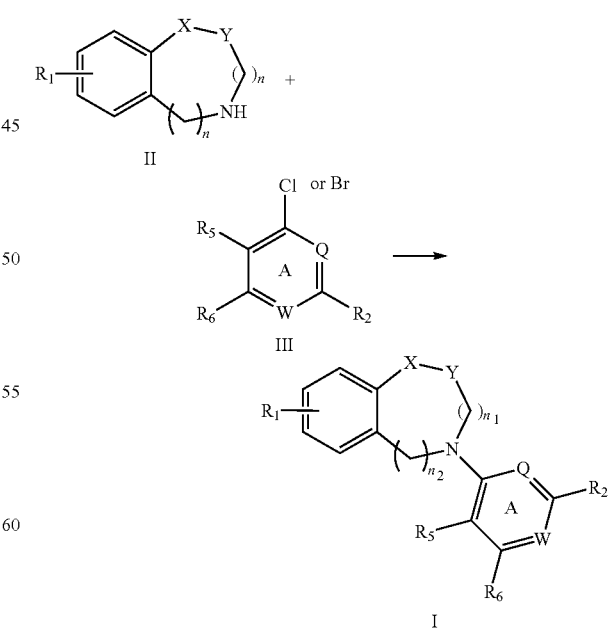

wherein $R_1$, $R_2$, $R_5$, $R_6$, X, Y, Q, W, $n_1$ and $n_2$ are defined as in claim 1, and optionally, converting the obtained compound of Formula I into a pharmaceutically acceptable salt thereof.

5. A method for treatment of a disease or disorder or alleviating severity of the disease or disorder, the method comprising administering to a patient in need of such treatment a therapeutically effective amount if at least one compound according to any one of claims 2 and 1 or a pharmaceutically acceptable salt thereof, wherein the disease or disorder is selected from lung cancer, prostate cancer, and nasopharyngeal cancer.

* * * * *